(12) United States Patent
Meridew

(10) Patent No.: US 8,308,810 B2
(45) Date of Patent: Nov. 13, 2012

(54) MULTIPLE BEARING ACETABULAR PROSTHESIS

(75) Inventor: Jason D. Meridew, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 226 days.

(21) Appl. No.: 12/502,848

(22) Filed: Jul. 14, 2009

(65) Prior Publication Data

US 2011/0015753 A1   Jan. 20, 2011

(51) Int. Cl.
*A61F 2/32* (2006.01)
(52) U.S. Cl. .................. 623/22.19; 623/22.28
(58) Field of Classification Search ............... 623/22.19, 623/22.2, 22.28, 22.29
See application file for complete search history.

(56) References Cited

U.S. PATENT DOCUMENTS

| | | |
|---|---|---|
| 3,584,318 A | 6/1971 | Scales et al. |
| 3,744,061 A | 7/1973 | Frost |
| 3,806,960 A | 4/1974 | Weber |
| 3,818,512 A | 6/1974 | Shersher |
| 3,859,669 A | 1/1975 | Shersher |
| 3,894,297 A | 7/1975 | Mittelmeier et al. |
| 4,001,897 A | 1/1977 | Rambert et al. |
| 4,031,570 A | 6/1977 | Frey |
| 4,058,856 A | 11/1977 | Doerre et al. |
| D249,957 S | 10/1978 | Eicher et al. |
| 4,172,296 A | 10/1979 | D'Errico |
| 4,241,463 A | 12/1980 | Khovaylo |
| 4,408,360 A | 10/1983 | Keller |
| 4,596,580 A | 6/1986 | Weill |
| 4,624,674 A | 11/1986 | Pappas et al. |
| 4,650,491 A | 3/1987 | Parchinski |
| 4,666,448 A | 5/1987 | Ganz |
| 4,666,450 A | 5/1987 | Kenna |
| 4,676,798 A | 6/1987 | Noiles |
| 4,676,799 A | 6/1987 | Legrand |
| 4,678,472 A | 7/1987 | Noiles |
| 4,681,589 A | 7/1987 | Tronzo |
| 4,687,487 A | 8/1987 | Hintermann |
| 4,693,986 A | 9/1987 | Vit et al. |
| 4,695,282 A | 9/1987 | Forte et al. |

(Continued)

FOREIGN PATENT DOCUMENTS

AU   770273 B2   2/2004

(Continued)

OTHER PUBLICATIONS

Biomer, "Biomechanical aspects of modular inlay fixation" (1997).

(Continued)

*Primary Examiner* — Bruce E Snow
(74) *Attorney, Agent, or Firm* — Harness, Dickey

(57) ABSTRACT

An acetabular prosthesis assembly can include an acetabular cup and a first liner. The acetabular cup can have an outer surface, an inner surface and an upper rim extending between the outer surface and the inner surface. The acetabular cup can have a cup connection portion including a groove formed on an upper face of the upper rim. The first liner can have an outer cup engaging surface and a liner connection portion that extends from a flange of the first liner. The liner connection portion can have a finger that is received by the groove formed on the upper face of the acetabular cup that selectively couples the liner connection portion with the cup connection portion in an assembled position.

19 Claims, 15 Drawing Sheets

U.S. PATENT DOCUMENTS

| | | | |
|---|---|---|---|
| 4,704,127 A | 11/1987 | Averill et al. | |
| 4,714,477 A | 12/1987 | Fichera et al. | |
| 4,715,859 A | 12/1987 | Schelhas et al. | |
| 4,715,860 A | 12/1987 | Amstutz et al. | |
| 4,716,894 A | 1/1988 | Lazzeri et al. | |
| 4,718,911 A | 1/1988 | Kenna | |
| 4,737,411 A | 4/1988 | Graves, Jr. et al. | |
| 4,743,262 A | 5/1988 | Tronzo | |
| 4,770,658 A | 9/1988 | Geremakis | |
| 4,770,659 A | 9/1988 | Kendall | |
| 4,784,662 A | 11/1988 | Muller | |
| 4,784,663 A | 11/1988 | Kenna | |
| 4,792,337 A | 12/1988 | Müller | |
| 4,795,469 A | 1/1989 | Oh | |
| 4,795,471 A | 1/1989 | Oh | |
| 4,801,301 A | 1/1989 | Noiles | |
| 4,813,961 A | 3/1989 | Sostegni | |
| 4,822,369 A | 4/1989 | Oueveau et al. | |
| 4,828,565 A | 5/1989 | Duthoit et al. | |
| 4,840,630 A | 6/1989 | Kitamura | |
| 4,840,632 A | 6/1989 | Kampner | |
| 4,841,975 A | 6/1989 | Woolson | |
| 4,851,006 A | 7/1989 | Tuke | |
| 4,871,368 A | 10/1989 | Wagner | |
| 4,878,916 A | 11/1989 | Rhenter et al. | |
| 4,883,491 A | 11/1989 | Mallory et al. | |
| 4,892,549 A | 1/1990 | Figgie, III et al. | |
| 4,904,265 A | 2/1990 | MacCollum et al. | |
| 4,908,033 A | 3/1990 | Frey et al. | |
| 4,911,723 A | 3/1990 | Menschik | |
| 4,919,674 A | 4/1990 | Schelhas | |
| 4,921,500 A | 5/1990 | Averill et al. | |
| 4,923,473 A | 5/1990 | Griss et al. | |
| 4,936,855 A | 6/1990 | Sherman | |
| 4,936,856 A | 6/1990 | Keller | |
| 4,936,861 A | 6/1990 | Muller et al. | |
| 4,950,299 A | 8/1990 | Noiles | |
| 4,955,325 A | 9/1990 | Zarnowski et al. | |
| 4,955,917 A | 9/1990 | Karpf | |
| 4,957,510 A | 9/1990 | Cremascoli | |
| 4,960,427 A | 10/1990 | Noiles | |
| 4,963,154 A | 10/1990 | Anapliotis et al. | |
| 4,969,910 A | 11/1990 | Frey et al. | |
| 4,978,356 A | 12/1990 | Noiles | |
| 4,994,064 A | 2/1991 | Aboczky | |
| 5,002,577 A | 3/1991 | Bolesky et al. | |
| 5,007,933 A | 4/1991 | Sidebotham et al. | |
| 5,019,105 A | 5/1991 | Wiley | |
| 5,021,062 A | 6/1991 | Adrey et al. | |
| 5,021,063 A | 6/1991 | Tager | |
| 5,030,221 A | 7/1991 | Buechel et al. | |
| 5,037,424 A | 8/1991 | Aboczsky | |
| 5,041,140 A | 8/1991 | Teinturier | |
| 5,049,158 A | 9/1991 | Engelhardt et al. | |
| 5,061,270 A | 10/1991 | Aboczky | |
| 5,062,853 A | 11/1991 | Forte | |
| 5,080,677 A | 1/1992 | Shelley | |
| 5,080,678 A | 1/1992 | Spotorno et al. | |
| 5,092,897 A | 3/1992 | Forte | |
| 5,092,898 A | 3/1992 | Bekki et al. | |
| 5,098,437 A | 3/1992 | Kashuba et al. | |
| 5,108,445 A | 4/1992 | Ashby | |
| 5,108,446 A | 4/1992 | Wagner et al. | |
| 5,108,447 A | 4/1992 | Zeiler et al. | |
| 5,108,448 A | 4/1992 | Gautier | |
| 5,116,339 A | 5/1992 | Glock | |
| 5,133,763 A | 7/1992 | Mullers | |
| 5,133,764 A | 7/1992 | Pappas et al. | |
| 5,147,407 A | 9/1992 | Tager | |
| 5,156,626 A | 10/1992 | Broderick et al. | |
| 5,169,399 A | 12/1992 | Ryland et al. | |
| 5,169,400 A | 12/1992 | Muhling et al. | |
| 5,171,285 A | 12/1992 | Broderick | |
| 5,171,286 A | 12/1992 | Lawes et al. | |
| 5,180,394 A | 1/1993 | Davidson | |
| 5,192,325 A | 3/1993 | Kijima et al. | |
| 5,222,984 A | 6/1993 | Forte | |
| 5,226,917 A * | 7/1993 | Schryver | 623/22.37 |
| 5,263,988 A | 11/1993 | Huebner | |
| 5,275,601 A | 1/1994 | Gogolewski et al. | |
| 5,282,864 A | 2/1994 | Noiles et al. | |
| 5,284,483 A | 2/1994 | Johnson et al. | |
| 5,310,408 A | 5/1994 | Schryver et al. | |
| 5,314,479 A | 5/1994 | Rockwood, Jr. et al. | |
| 5,314,487 A | 5/1994 | Schryver et al. | |
| 5,314,491 A | 5/1994 | Thongpreda et al. | |
| 5,326,368 A | 7/1994 | Collazo | |
| 5,358,532 A | 10/1994 | Evans et al. | |
| 5,360,451 A | 11/1994 | Keller | |
| 5,360,452 A | 11/1994 | Engelhardt et al. | |
| 5,364,403 A | 11/1994 | Petersen et al. | |
| 5,370,702 A | 12/1994 | Jones | |
| 5,376,122 A | 12/1994 | Pappas et al. | |
| 5,383,938 A | 1/1995 | Rohr et al. | |
| 5,405,392 A | 4/1995 | Deckner | |
| 5,405,502 A | 4/1995 | Palmu et al. | |
| 5,413,603 A | 5/1995 | Noiles et al. | |
| 5,417,696 A | 5/1995 | Kashuba et al. | |
| 5,425,778 A | 6/1995 | Zichner et al. | |
| 5,425,779 A | 6/1995 | Schlosser et al. | |
| 5,431,657 A | 7/1995 | Rohr | |
| 5,443,519 A | 8/1995 | Averill et al. | |
| 5,458,649 A | 10/1995 | Spotorno et al. | |
| 5,458,650 A | 10/1995 | Carret et al. | |
| 5,474,560 A | 12/1995 | Rohr, Jr. | |
| 5,480,448 A | 1/1996 | Mikhail | |
| 5,486,181 A | 1/1996 | Cohen et al. | |
| 5,507,824 A | 4/1996 | Lennox | |
| 5,507,825 A | 4/1996 | Frei | |
| 5,507,826 A | 4/1996 | Besselink et al. | |
| 5,507,828 A | 4/1996 | Maumy et al. | |
| 5,520,985 A | 5/1996 | Helicher | |
| 5,527,317 A | 6/1996 | Ashby et al. | |
| 5,534,027 A | 7/1996 | Hodorek | |
| 5,540,697 A | 7/1996 | Rehmann et al. | |
| 5,549,681 A | 8/1996 | Segmuller et al. | |
| 5,549,693 A | 8/1996 | Roux et al. | |
| 5,549,694 A | 8/1996 | Noiles et al. | |
| 5,549,696 A | 8/1996 | Willi | |
| 5,549,697 A | 8/1996 | Caldarise | |
| 5,549,698 A | 8/1996 | Averill et al. | |
| 5,549,699 A | 8/1996 | MacMahon et al. | |
| 5,549,700 A | 8/1996 | Graham et al. | |
| 5,549,701 A | 8/1996 | Mikhail | |
| 5,571,198 A | 11/1996 | Drucker et al. | |
| 5,571,200 A | 11/1996 | Cohen et al. | |
| 5,571,201 A | 11/1996 | Averill et al. | |
| 5,577,368 A | 11/1996 | Hamilton et al. | |
| 5,584,837 A | 12/1996 | Petersen | |
| 5,593,445 A | 1/1997 | Waits | |
| 5,609,647 A | 3/1997 | K alberer et al. | |
| 5,609,648 A | 3/1997 | Oehy et al. | |
| 5,624,464 A | 4/1997 | Wagner et al. | |
| 5,639,280 A | 6/1997 | Warner et al. | |
| 5,641,323 A | 6/1997 | Caldarise | |
| 5,645,594 A | 7/1997 | Devanathan et al. | |
| 5,645,601 A | 7/1997 | Pope et al. | |
| 5,645,606 A | 7/1997 | Oehy et al. | |
| 5,658,294 A | 8/1997 | Sederholm | |
| 5,658,338 A | 8/1997 | Tullos et al. | |
| 5,658,345 A | 8/1997 | Willi | |
| 5,658,346 A | 8/1997 | Willi | |
| 5,658,347 A | 8/1997 | Sarkisian et al. | |
| 5,658,348 A | 8/1997 | Rohr, Jr. | |
| 5,665,119 A | 9/1997 | Koller | |
| 5,676,704 A | 10/1997 | Ries et al. | |
| 5,690,632 A | 11/1997 | Schwartz et al. | |
| 5,702,448 A | 12/1997 | Buechel et al. | |
| 5,702,456 A | 12/1997 | Pienkowski | |
| 5,702,473 A | 12/1997 | Albrektsson et al. | |
| 5,702,475 A | 12/1997 | Zahedi | |
| 5,702,476 A | 12/1997 | Limacher et al. | |
| 5,702,477 A | 12/1997 | Capello et al. | |
| 5,702,478 A | 12/1997 | Tornier | |
| 5,702,483 A | 12/1997 | Kwong | |
| 5,711,973 A | 1/1998 | Rothschild et al. | |
| 5,716,414 A | 2/1998 | Caldarise | |

| | | | | | | |
|---|---|---|---|---|---|---|
| 5,725,580 | A | 3/1998 | Cloutier et al. | 6,162,856 A | 12/2000 | Crompton et al. |
| 5,725,587 | A | 3/1998 | Garber | 6,165,220 A | 12/2000 | McKellop et al. |
| 5,725,588 | A | 3/1998 | Errico et al. | 6,206,881 B1 | 3/2001 | Frigg et al. |
| 5,725,589 | A | 3/1998 | Pfaff et al. | 6,206,929 B1 | 3/2001 | Ochoa et al. |
| 5,725,591 | A | 3/1998 | DeCarlo, Jr. et al. | 6,217,615 B1 | 4/2001 | Sioshansi et al. |
| 5,752,958 | A | 5/1998 | Wellisz | 6,224,096 B1 | 5/2001 | Katsuda et al. |
| 5,755,799 | A | 5/1998 | Oehy et al. | 6,224,633 B1 | 5/2001 | Kalberer et al. |
| 5,755,803 | A | 5/1998 | Haines et al. | 6,228,121 B1 | 5/2001 | Khalili |
| 5,755,806 | A | 5/1998 | Stalcup et al. | 6,231,612 B1 | 5/2001 | Balay et al. |
| 5,755,808 | A | 5/1998 | DeCarlo et al. | 6,238,435 B1 | 5/2001 | Meulink et al. |
| 5,756,027 | A | 5/1998 | Rothschild et al. | 6,241,773 B1 | 6/2001 | Tashima et al. |
| 5,766,260 | A | 6/1998 | Whiteside | 6,248,132 B1 | 6/2001 | Harris |
| 5,766,280 | A | 6/1998 | Hallqvist et al. | 6,250,494 B1 * | 6/2001 | Diamond ..................... 220/783 |
| 5,768,134 | A | 6/1998 | Swaelens et al. | 6,280,476 B1 | 8/2001 | Metzger et al. |
| 5,782,928 | A | 7/1998 | Ries et al. | 6,306,140 B1 | 10/2001 | Siddiqui |
| 5,782,929 | A | 7/1998 | Sederholm | 6,319,257 B1 | 11/2001 | Carignan et al. |
| 5,782,930 | A | 7/1998 | Lin et al. | 6,319,285 B1 | 11/2001 | Chamier et al. |
| 5,788,916 | A | 8/1998 | Caldarise | 6,334,875 B1 | 1/2002 | Keller |
| 5,800,555 | A | 9/1998 | Gray, III | 6,352,559 B1 | 3/2002 | Church |
| 5,824,107 | A | 10/1998 | Tschirren | 6,355,043 B1 | 3/2002 | Adam |
| 5,824,108 | A | 10/1998 | Huebner | 6,358,282 B1 | 3/2002 | Wymann |
| 5,830,215 | A | 11/1998 | Incavo et al. | 6,368,354 B2 | 4/2002 | Burstein et al. |
| 5,871,547 | A | 2/1999 | Abouaf et al. | 6,379,389 B1 | 4/2002 | Koch |
| 5,871,548 | A | 2/1999 | Sanders et al. | 6,387,132 B1 | 5/2002 | Deppisch et al. |
| 5,879,297 | A | 3/1999 | Haynor et al. | 6,395,005 B1 | 5/2002 | Lovell |
| 5,879,397 | A | 3/1999 | Kalberer et al. | 6,416,553 B1 | 7/2002 | White et al. |
| 5,879,398 | A | 3/1999 | Swarts et al. | 6,420,568 B1 | 7/2002 | Matson et al. |
| 5,879,399 | A | 3/1999 | Church | 6,425,921 B1 | 7/2002 | Grundei et al. |
| 5,879,400 | A | 3/1999 | Merrill et al. | 6,447,550 B1 | 9/2002 | Hunter et al. |
| 5,879,401 | A | 3/1999 | Besemer et al. | 6,454,809 B1 | 9/2002 | Tornier |
| 5,879,402 | A | 3/1999 | Lawes et al. | 6,468,281 B1 | 10/2002 | Badorf et al. |
| 5,879,404 | A | 3/1999 | Bateman et al. | 6,475,243 B1 | 11/2002 | Sheldon et al. |
| 5,879,405 | A | 3/1999 | Ries et al. | 6,488,713 B1 | 12/2002 | Hershberger |
| 5,879,406 | A | 3/1999 | Lilley | 6,488,715 B1 | 12/2002 | Pope et al. |
| 5,879,407 | A | 3/1999 | Waggener | 6,517,583 B1 | 2/2003 | Pope et al. |
| 5,885,299 | A | 3/1999 | Winslow et al. | 6,520,995 B2 | 2/2003 | Church |
| 5,888,204 | A | 3/1999 | Ralph et al. | 6,527,808 B1 | 3/2003 | Albertorio et al. |
| 5,888,205 | A | 3/1999 | Pratt et al. | 6,527,809 B1 | 3/2003 | Doursounian et al. |
| 5,897,592 | A | 4/1999 | Caldarise et al. | 6,537,321 B1 | 3/2003 | Horber |
| 5,904,688 | A | 5/1999 | Gilbert et al. | 6,558,794 B1 | 5/2003 | Fehrenbacher et al. |
| 5,904,720 | A | 5/1999 | Farrar et al. | 6,575,980 B1 | 6/2003 | Robie et al. |
| 5,916,268 | A | 6/1999 | Schollner et al. | 6,589,284 B1 | 7/2003 | Silberer |
| 5,916,270 | A | 6/1999 | Lipman | 6,609,599 B1 | 8/2003 | Chang |
| 5,919,236 | A | 7/1999 | Pfaff et al. | 6,609,621 B2 | 8/2003 | Denny et al. |
| 5,931,870 | A | 8/1999 | Cuckler et al. | 6,610,097 B2 | 8/2003 | Serbousek et al. |
| 5,935,175 | A | 8/1999 | Ostiguy, Jr. et al. | 6,610,257 B2 | 8/2003 | Vane |
| 5,938,701 | A | 8/1999 | Hiernard et al. | 6,611,636 B2 | 8/2003 | Deliwala |
| 5,938,702 | A | 8/1999 | Lopez et al. | 6,611,816 B2 | 8/2003 | Lebda et al. |
| 5,964,809 | A | 10/1999 | Lin et al. | 6,611,862 B2 | 8/2003 | Reisman |
| 5,972,032 | A | 10/1999 | Lopez et al. | 6,611,973 B2 | 9/2003 | Connell |
| 5,989,293 | A | 11/1999 | Cook et al. | 6,612,256 B1 | 9/2003 | Martin |
| 5,989,294 | A | 11/1999 | Marlow | 6,612,384 B1 | 9/2003 | Singh et al. |
| 5,997,579 | A | 12/1999 | Albrektsson et al. | 6,612,417 B2 | 9/2003 | Garvey |
| 6,013,082 | A | 1/2000 | Hiernard et al. | 6,612,425 B1 | 9/2003 | Garvey |
| 6,013,104 | A | 1/2000 | Kampner | 6,612,430 B1 | 9/2003 | Silvera |
| 6,022,357 | A | 2/2000 | Reu et al. | 6,612,545 B1 | 9/2003 | Rutter et al. |
| 6,027,505 | A | 2/2000 | Peter et al. | 6,612,649 B2 | 9/2003 | Kain |
| 6,045,583 | A | 4/2000 | Gross et al. | 6,612,713 B1 | 9/2003 | Kuelbs |
| 6,051,751 | A | 4/2000 | Sioshansi et al. | 6,612,766 B2 | 9/2003 | Collins |
| 6,059,833 | A | 5/2000 | Doets | 6,613,235 B1 | 9/2003 | Anderson, Jr. et al. |
| 6,063,123 | A | 5/2000 | Burrows et al. | 6,615,535 B2 | 9/2003 | Snell et al. |
| 6,063,124 | A | 5/2000 | Amstutz | 6,615,756 B2 | 9/2003 | Barrus |
| 6,087,553 | A | 7/2000 | Cohen et al. | 6,615,766 B1 | 9/2003 | Curry |
| 6,093,208 | A | 7/2000 | Tian | 6,616,310 B1 | 9/2003 | Marsh |
| 6,096,083 | A | 8/2000 | Keller et al. | 6,616,498 B1 | 9/2003 | Thai |
| 6,102,951 | A | 8/2000 | Sutter et al. | 6,616,924 B1 | 9/2003 | Chastain |
| 6,105,235 | A | 8/2000 | Caldarise | 6,618,047 B1 | 9/2003 | Lim |
| 6,120,545 | A | 9/2000 | Hamelijnck et al. | 6,618,157 B2 | 9/2003 | Coyle et al. |
| 6,120,546 | A | 9/2000 | Dye et al. | 6,618,753 B2 | 9/2003 | Holland et al. |
| 6,126,695 | A | 10/2000 | Semlitsch | 6,618,806 B1 | 9/2003 | Brown et al. |
| 6,129,730 | A | 10/2000 | Bono et al. | 6,619,167 B2 | 9/2003 | Mikkelsen et al. |
| 6,129,765 | A | 10/2000 | Lopez et al. | 6,619,168 B2 | 9/2003 | Alsten et al. |
| 6,136,033 | A | 10/2000 | Suemer | 6,619,235 B2 | 9/2003 | Woytowitz, Jr. |
| 6,136,034 | A | 10/2000 | Townley | 6,619,331 B1 | 9/2003 | Suchdev |
| 6,139,582 | A | 10/2000 | DeCarlo, Jr. et al. | 6,619,594 B2 | 9/2003 | Wolf et al. |
| 6,152,930 | A | 11/2000 | Mastrorio | 6,619,603 B1 | 9/2003 | Recknagel et al. |
| 6,152,961 | A | 11/2000 | Ostiguy, Jr. et al. | 6,619,808 B1 | 9/2003 | Pelto |
| 6,152,962 | A | 11/2000 | DeCarlo, Jr. | 6,619,816 B1 | 9/2003 | Johnson |
| 6,162,256 | A | 12/2000 | Ostiguy, Jr. et al. | 6,620,016 B1 | 9/2003 | Thai |

| Patent Number | Date | Name |
|---|---|---|
| 6,620,046 B2 | 9/2003 | Rowe |
| 6,620,319 B2 | 9/2003 | Behmann et al. |
| 6,621,083 B2 | 9/2003 | Cole |
| 6,621,172 B2 | 9/2003 | Nakayama et al. |
| 6,621,515 B2 | 9/2003 | Matthews et al. |
| 6,621,834 B1 | 9/2003 | Scherpbier et al. |
| 6,622,128 B1 | 9/2003 | Bedell et al. |
| 6,622,327 B1 | 9/2003 | Rivera |
| 6,622,328 B2 | 9/2003 | Rivera |
| 6,622,350 B2 | 9/2003 | Austin et al. |
| 6,622,414 B1 | 9/2003 | Oliver et al. |
| 6,622,858 B1 | 9/2003 | Wilkinson et al. |
| 6,623,354 B2 | 9/2003 | Morris et al. |
| 6,626,913 B1 | 9/2003 | McKinnon et al. |
| 6,626,947 B2 | 9/2003 | Lester et al. |
| 6,638,311 B2 | 10/2003 | Wang et al. |
| 6,641,617 B1 | 11/2003 | Merrill et al. |
| 6,652,533 B2 | 11/2003 | O'Neil |
| 6,652,586 B2 | 11/2003 | Hunter et al. |
| 6,660,040 B2 | 12/2003 | Chan et al. |
| RE38,409 E | 1/2004 | Noiles |
| 6,676,706 B1 | 1/2004 | Mears et al. |
| 6,682,566 B2 | 1/2004 | Draenert |
| 6,706,071 B1 | 3/2004 | Wolter |
| 6,709,462 B2 | 3/2004 | Hanssen |
| 6,712,857 B1 | 3/2004 | Roger |
| 6,726,725 B2 | 4/2004 | Hunter et al. |
| 6,730,091 B1 | 5/2004 | Pfefferle et al. |
| 6,746,454 B2 | 6/2004 | Winterbottom et al. |
| 6,755,835 B2 | 6/2004 | Schultheiss et al. |
| 6,758,864 B2 | 7/2004 | Storer et al. |
| 6,761,741 B2 | 7/2004 | Iesaka |
| 6,797,007 B1 | 9/2004 | Von Chamier et al. |
| 6,811,569 B1 | 11/2004 | Afriat et al. |
| 6,821,278 B2 | 11/2004 | Frigg et al. |
| 6,827,742 B2 | 12/2004 | Hayes, Jr. et al. |
| 6,860,903 B2 | 3/2005 | Mears et al. |
| 6,866,685 B2 | 3/2005 | Chan et al. |
| 6,881,229 B2 | 4/2005 | Khandkar et al. |
| 6,916,342 B2 | 7/2005 | Frederick et al. |
| 6,926,740 B2 | 8/2005 | Lewis et al. |
| 7,160,332 B2 | 1/2007 | Frederick et al. |
| 7,264,636 B2 | 9/2007 | Lewis et al. |
| 7,294,150 B1 | 11/2007 | Mandell et al. |
| RE40,090 E | 2/2008 | Whiteside |
| 7,326,253 B2 | 2/2008 | Synder et al. |
| 7,507,063 B2 | 3/2009 | Dexter et al. |
| 7,794,504 B2 | 9/2010 | Case |
| 7,819,925 B2 | 10/2010 | King et al. |
| 7,955,395 B2 | 6/2011 | Shea et al. |
| 2001/0037156 A1 | 11/2001 | Burstein et al. |
| 2001/0051830 A1 | 12/2001 | Tuke et al. |
| 2002/0040244 A1 | 4/2002 | Despres et al. |
| 2002/0040245 A1 | 4/2002 | Lester et al. |
| 2002/0045901 A1 | 4/2002 | Wagner et al. |
| 2002/0049500 A1 | 4/2002 | Draenert |
| 2002/0052659 A1 | 5/2002 | Hayes et al. |
| 2002/0058988 A1 | 5/2002 | Fischell et al. |
| 2002/0058998 A1 | 5/2002 | Church |
| 2002/0068980 A1 | 6/2002 | Serbousek et al. |
| 2002/0107577 A1 | 8/2002 | Storer et al. |
| 2002/0111691 A1 | 8/2002 | Wang et al. |
| 2002/0116068 A1 | 8/2002 | McLean |
| 2002/0143402 A1 | 10/2002 | Steinberg |
| 2002/0147499 A1 | 10/2002 | Shea et al. |
| 2002/0156536 A1 | 10/2002 | Harris et al. |
| 2002/0165615 A1 | 11/2002 | Abouaf et al. |
| 2002/0177854 A1 | 11/2002 | Tuke et al. |
| 2003/0050645 A1 | 3/2003 | Parker et al. |
| 2003/0050703 A1 | 3/2003 | Harris et al. |
| 2003/0050705 A1 | 3/2003 | Cueille et al. |
| 2003/0060889 A1 | 3/2003 | Tarabishy |
| 2003/0060890 A1 | 3/2003 | Tarabishy |
| 2003/0105529 A1 | 6/2003 | Synder et al. |
| 2003/0120347 A1 | 6/2003 | Steinberg |
| 2003/0135281 A1 | 7/2003 | Hanssen |
| 2003/0149438 A1 | 8/2003 | Nichols et al. |
| 2003/0153981 A1 | 8/2003 | Wang et al. |
| 2003/0153982 A1 | 8/2003 | Pria |
| 2003/0158559 A1 | 8/2003 | Diaz |
| 2003/0163203 A1 | 8/2003 | Nycz et al. |
| 2003/0171817 A1 | 9/2003 | Rambert et al. |
| 2003/0187512 A1 | 10/2003 | Frederick et al. |
| 2003/0191537 A1 | 10/2003 | Wasielewski |
| 2003/0212458 A1 | 11/2003 | Harris et al. |
| 2003/0229356 A1 | 12/2003 | Dye |
| 2003/0233100 A1 | 12/2003 | Santarella et al. |
| 2004/0002766 A1 | 1/2004 | Hunter et al. |
| 2004/0019380 A1 | 1/2004 | Baege et al. |
| 2004/0023784 A1 | 2/2004 | Yu et al. |
| 2004/0030344 A1 | 2/2004 | Dye et al. |
| 2004/0034352 A1 | 2/2004 | Needham et al. |
| 2004/0054373 A1 | 3/2004 | Serra et al. |
| 2004/0054418 A1 | 3/2004 | McLean et al. |
| 2004/0059427 A1 | 3/2004 | Serbousek et al. |
| 2004/0059429 A1 | 3/2004 | Amin et al. |
| 2004/0073225 A1 | 4/2004 | Subba Rao |
| 2004/0073226 A1 | 4/2004 | Cotting et al. |
| 2004/0088052 A1 | 5/2004 | Dearnaley |
| 2004/0098127 A1 | 5/2004 | Charlebois et al. |
| 2004/0111089 A1 | 6/2004 | Stevens et al. |
| 2004/0122524 A1 | 6/2004 | Hunter et al. |
| 2004/0143341 A1 | 7/2004 | McLean |
| 2004/0158330 A1 | 8/2004 | Muller et al. |
| 2004/0172039 A1 | 9/2004 | Dye |
| 2004/0186586 A1 | 9/2004 | Seyer et al. |
| 2004/0199258 A1 | 10/2004 | Macara |
| 2004/0204767 A1 | 10/2004 | Park et al. |
| 2004/0215200 A1 | 10/2004 | Tornier et al. |
| 2004/0220679 A1 | 11/2004 | Diaz et al. |
| 2004/0225369 A1 | 11/2004 | Lakin et al. |
| 2004/0225370 A1 | 11/2004 | Cruchet et al. |
| 2004/0225371 A1 | 11/2004 | Roger |
| 2004/0236341 A1 | 11/2004 | Petersen |
| 2004/0241314 A1 | 12/2004 | Li |
| 2004/0267373 A1 | 12/2004 | Dwyer et al. |
| 2004/0267376 A1 | 12/2004 | Suzuki et al. |
| 2005/0004678 A1 | 1/2005 | Richards |
| 2005/0010303 A1 | 1/2005 | Nogier |
| 2005/0033442 A1 | 2/2005 | Fisher et al. |
| 2005/0033445 A1 | 2/2005 | Siebel |
| 2005/0060040 A1 | 3/2005 | Auxepaules et al. |
| 2005/0065527 A1 | 3/2005 | Justin |
| 2005/0070904 A1 | 3/2005 | Gerlach et al. |
| 2005/0071015 A1 | 3/2005 | Sekel |
| 2005/0080490 A1 | 4/2005 | Bertram |
| 2005/0085820 A1 | 4/2005 | Collins et al. |
| 2005/0085823 A1 | 4/2005 | Murphy |
| 2005/0087915 A1 | 4/2005 | Pope et al. |
| 2005/0090903 A1 | 4/2005 | Khandkar et al. |
| 2005/0102034 A1 | 5/2005 | Hayes et al. |
| 2005/0102035 A1 | 5/2005 | Grundei |
| 2005/0240276 A1 | 10/2005 | Shea et al. |
| 2005/0246031 A1 | 11/2005 | Frederick et al. |
| 2006/0004463 A1 | 1/2006 | Lewis et al. |
| 2006/0178750 A1 | 8/2006 | Chieng |
| 2006/0229731 A1 | 10/2006 | Newsome et al. |
| 2006/0276905 A1 | 12/2006 | Calamel |
| 2007/0106352 A1 | 5/2007 | Carstens |
| 2007/0106392 A1 | 5/2007 | Servidio et al. |
| 2007/0173948 A1 | 7/2007 | Meridew et al. |
| 2007/0203583 A1 | 8/2007 | Slone |
| 2007/0203585 A1 | 8/2007 | Wilson |
| 2007/0239283 A1 | 10/2007 | Berger et al. |
| 2008/0140215 A1 | 6/2008 | Gladdish et al. |
| 2009/0008886 A1 | 1/2009 | Shu |
| 2009/0088865 A1 | 4/2009 | Brehm |
| 2009/0101776 A1 | 4/2009 | Peterson et al. |
| 2009/0287312 A1 | 11/2009 | Berger et al. |
| 2010/0262144 A1 | 10/2010 | Kelman et al. |
| 2011/0009975 A1 | 1/2011 | Allen et al. |
| 2011/0087335 A1 | 4/2011 | Newsome et al. |

FOREIGN PATENT DOCUMENTS

| | | |
|---|---|---|
| AU | 2003266434 A1 | 7/2004 |
| AU | 781574 B2 | 6/2005 |
| AU | 2005221715 A1 | 9/2005 |
| AU | 783205 B2 | 10/2005 |

| | | | | | | |
|---|---|---|---|---|---|---|
| AU | 2002336155 B2 | 11/2006 | | EP | 0636351 A2 | 2/1995 |
| AU | 2006340337 A1 | 9/2007 | | EP | 0639357 A1 | 2/1995 |
| AU | 2007333133 A1 | 6/2008 | | EP | 0645984 A1 | 4/1995 |
| AU | 2002302005 B2 | 8/2008 | | EP | 0648478 | 4/1995 |
| AU | 2008218993 A1 | 8/2008 | | EP | 0649641 A2 | 4/1995 |
| AU | 2008242972 A1 | 10/2008 | | EP | 0654255 A1 | 5/1995 |
| AU | 2009202628 A1 | 1/2010 | | EP | 0663193 A1 | 7/1995 |
| AU | 2009286494 A1 | 3/2010 | | EP | 0680735 A2 | 11/1995 |
| CA | 2061183 A1 | 8/1992 | | EP | 0694294 A1 | 1/1996 |
| CA | 2314497 A1 | 6/1999 | | EP | 0699425 A1 | 3/1996 |
| CH | 554668 A | 10/1974 | | EP | 0714644 A1 | 6/1996 |
| DE | 1975536 U | 12/1967 | | EP | 0722703 A2 | 7/1996 |
| DE | 2950536 A1 | 7/1981 | | EP | 0726066 A2 | 8/1996 |
| DE | 8500869 U1 | 12/1985 | | EP | 0728448 A1 | 8/1996 |
| DE | 3535959 C1 | 4/1987 | | EP | 0743049 A1 | 11/1996 |
| DE | 3726213 A1 | 2/1989 | | EP | 0743050 A1 | 11/1996 |
| DE | 4102510 A1 | 7/1992 | | EP | 0771552 A1 | 5/1997 |
| DE | 4106272 A1 | 9/1992 | | EP | 0773007 A1 | 5/1997 |
| DE | 9208752 U1 | 12/1992 | | EP | 0826347 A1 | 3/1998 |
| DE | 4128259 A1 | 3/1993 | | EP | 0841041 A2 | 5/1998 |
| DE | 4142920 A1 | 7/1993 | | EP | 0927547 A2 | 7/1999 |
| DE | 4211345 C1 | 11/1993 | | EP | 0927548 A2 | 7/1999 |
| DE | 4219939 | 12/1993 | | EP | 0941718 A2 | 9/1999 |
| DE | 4222218 A1 | 1/1994 | | EP | 0944368 A1 | 9/1999 |
| DE | 4304022 A1 | 8/1994 | | EP | 0945109 A2 | 9/1999 |
| DE | 9418900 U1 | 1/1995 | | EP | 0949891 A1 | 10/1999 |
| DE | 4325701 A1 | 2/1995 | | EP | 0958797 A1 | 11/1999 |
| DE | 4336552 C1 | 3/1995 | | EP | 0995412 A1 | 4/2000 |
| DE | 4335931 A1 | 4/1995 | | EP | 1013241 A2 | 6/2000 |
| DE | 29516473 U1 | 12/1995 | | EP | 1052949 A1 | 11/2000 |
| DE | 29517637 U1 | 1/1996 | | EP | 1066806 A1 | 1/2001 |
| DE | 19616058 A1 | 10/1997 | | EP | 1086666 A1 | 3/2001 |
| DE | 19616059 A1 | 10/1997 | | EP | 1098611 A1 | 5/2001 |
| DE | 19620750 C1 | 1/1998 | | EP | 1308141 A1 | 5/2003 |
| DE | 19701536 A1 | 2/1998 | | EP | 1312323 A2 | 5/2003 |
| DE | 19654409 C1 | 4/1998 | | EP | 1336394 A1 | 8/2003 |
| DE | 19701778 A1 | 6/1998 | | EP | 1395206 A1 | 3/2004 |
| DE | 19755776 A1 | 7/1999 | | EP | 1610729 A1 | 1/2006 |
| DE | 19755246 C1 | 3/2000 | | EP | 1631219 A2 | 3/2006 |
| DE | 19919083 C1 | 12/2000 | | EP | 1712206 A2 | 10/2006 |
| DE | 20201785 U1 | 6/2002 | | EP | 1813227 A2 | 8/2007 |
| DE | 102010001600 A1 | 8/2010 | | EP | 1825834 | 8/2007 |
| EP | 0066092 A1 | 12/1982 | | EP | 2193764 A1 | 6/2010 |
| EP | 0091315 A1 | 10/1983 | | FR | 2419717 A1 | 10/1979 |
| EP | 0137664 A2 | 4/1985 | | FR | 2592787 A1 | 7/1987 |
| EP | 0139356 A1 | 5/1985 | | FR | 2597329 A1 | 10/1987 |
| EP | 169978 A1 | 2/1986 | | FR | 2617040 A1 | 12/1988 |
| EP | 0190093 A1 | 8/1986 | | FR | 2628314 A1 | 9/1989 |
| EP | 0208578 A1 | 1/1987 | | FR | 2628967 A1 | 9/1989 |
| EP | 0214885 | 3/1987 | | FR | 2631542 A1 | 11/1989 |
| EP | 0239210 A1 | 9/1987 | | FR | 2638963 A1 | 5/1990 |
| EP | 0239485 A2 | 9/1987 | | FR | 2648703 A1 | 12/1990 |
| EP | 0245527 A1 | 11/1987 | | FR | 2653326 A1 | 4/1991 |
| EP | 0265712 A1 | 5/1988 | | FR | 2661605 A1 | 11/1991 |
| EP | 0270744 A1 | 6/1988 | | FR | 2668055 A1 | 4/1992 |
| EP | 0297789 A1 | 1/1989 | | FR | 2668057 A1 | 4/1992 |
| EP | 0302850 A2 | 2/1989 | | FR | 2668923 A1 | 5/1992 |
| EP | 0313762 A1 | 5/1989 | | FR | 2680674 A1 | 3/1993 |
| EP | 0315795 A1 | 5/1989 | | FR | 2682588 A1 | 4/1993 |
| EP | 0329019 A1 | 8/1989 | | FR | 2684544 A1 | 6/1993 |
| EP | 0341199 A1 | 11/1989 | | FR | 2699067 A1 | 6/1994 |
| EP | 0346270 A1 | 12/1989 | | FR | 2700686 A1 | 7/1994 |
| EP | 0357302 A1 | 3/1990 | | FR | 2700946 A1 | 8/1994 |
| EP | 0402810 A1 | 12/1990 | | FR | 2708459 A1 | 2/1995 |
| EP | 0404680 A1 | 12/1990 | | FR | 2715828 A3 | 8/1995 |
| EP | 0407332 A1 | 1/1991 | | FR | 2719761 A1 | 11/1995 |
| EP | 0436317 A1 | 7/1991 | | FR | 2728157 A1 | 6/1996 |
| EP | 0444381 A1 | 9/1991 | | FR | 2748654 A1 | 11/1997 |
| EP | 0453694 A1 | 10/1991 | | FR | 2748655 A1 | 11/1997 |
| EP | 0482320 A1 | 4/1992 | | FR | 2793137 A1 | 11/2000 |
| EP | 0485678 A1 | 5/1992 | | FR | 2824258 A1 | 11/2002 |
| EP | 0488943 A1 | 6/1992 | | FR | 2846225 A1 | 4/2004 |
| EP | 0498685 A1 | 8/1992 | | FR | 2847801 A1 | 6/2004 |
| EP | 0501207 A1 | 9/1992 | | FR | 2897527 A1 | 8/2007 |
| EP | 0554214 A1 | 8/1993 | | GB | 1245451 A | 9/1971 |
| EP | 0578322 A2 | 1/1994 | | GB | 2029229 A | 3/1980 |
| EP | 0578345 A1 | 1/1994 | | GB | 2316873 A | 3/1998 |
| EP | 0586335 A1 | 3/1994 | | GB | 2358353 A | 7/2001 |
| EP | 0610146 A1 | 8/1994 | | GB | 2365343 A | 2/2002 |

| | | | |
|---|---|---|---|
| GB | 2463066 A | 3/2010 | |
| JP | 54127195 A | 10/1979 | |
| JP | 1136654 A | 5/1989 | |
| JP | 2161943 A | 6/1990 | |
| JP | 3029650 A | 2/1991 | |
| JP | 5068690 A | 3/1993 | |
| JP | 5137738 A | 6/1993 | |
| JP | 5208027 A | 8/1993 | |
| JP | 716248 | 1/1995 | |
| JP | 7144004 A | 6/1995 | |
| JP | 10146351 A | 6/1998 | |
| JP | 10216162 A | 8/1998 | |
| JP | 11253470 A | 9/1999 | |
| JP | 11313843 A | 11/1999 | |
| JP | 11347055 | 12/1999 | |
| JP | 2001286496 A | 10/2001 | |
| JP | 2009530021 A | 8/2009 | |
| WO | WO-8602261 A1 | 4/1986 | |
| WO | WO-9218067 A1 | 10/1992 | |
| WO | WO-9222265 A1 | 12/1992 | |
| WO | WO-9325157 A1 | 12/1993 | |
| WO | WO-9405234 A1 | 3/1994 | |
| WO | WO-9423670 A1 | 10/1994 | |
| WO | WO-9516413 A1 | 6/1995 | |
| WO | WO-9517140 A1 | 6/1995 | |
| WO | WO-9522944 A1 | 8/1995 | |
| WO | WO-9523566 A1 | 9/1995 | |
| WO | WO-9604862 A1 | 2/1996 | |
| WO | WO-9604866 A1 | 2/1996 | |
| WO | WO-9604867 A1 | 2/1996 | |
| WO | WO-9613231 A1 | 5/1996 | |
| WO | WO-9623457 A1 | 8/1996 | |
| WO | WO-9717040 A1 | 5/1997 | |
| WO | WO-9742913 A1 | 11/1997 | |
| WO | WO-9815240 A1 | 4/1998 | |
| WO | WO-9822049 A1 | 5/1998 | |
| WO | WO-9922674 A1 | 5/1999 | |
| WO | WO-9925276 A1 | 5/1999 | |
| WO | WO-9930634 A2 | 6/1999 | |
| WO | WO-9960955 A1 | 12/1999 | |
| WO | WO-0009045 A1 | 2/2000 | |
| WO | WO-0045748 A1 | 8/2000 | |
| WO | WO-0076427 A1 | 12/2000 | |
| WO | WO-0124739 A2 | 4/2001 | |
| WO | WO-0132108 A1 | 5/2001 | |
| WO | WO-0176511 A1 | 10/2001 | |
| WO | WO-02102285 A1 | 12/2002 | |
| WO | WO-03011116 A2 | 2/2003 | |
| WO | WO-03047470 A2 | 6/2003 | |
| WO | WO-2004084772 A1 | 10/2004 | |
| WO | WO-2004110318 A2 | 12/2004 | |
| WO | WO-2005087141 A2 | 9/2005 | |
| WO | WO-2007056678 A2 | 5/2007 | |
| WO | WO-2007/108848 A1 | 9/2007 | |
| WO | WO-2007121167 A1 | 10/2007 | |
| WO | WO-2008073946 A2 | 6/2008 | |
| WO | WO-2008103457 A2 | 8/2008 | |
| WO | WO-2008130989 A2 | 10/2008 | |
| WO | WO-2008146121 A2 | 12/2008 | |
| WO | WO-2009097412 A2 | 8/2009 | |
| WO | WO-2010023447 A1 | 3/2010 | |
| WO | WO-2010060071 A1 | 5/2010 | |
| WO | WO-2011008757 A1 | 1/2011 | |

OTHER PUBLICATIONS

Ceraver, The Answer-Ceral AI203-AI203 Combination.

International Search Report and Written Opinion mailed Oct. 14, 2010 claiming benefit of U.S. Appl. No. 12/502,848, filed Jul. 14, 2009.

JRI, "The Original Furlong Hydroxapatite Ceramic (Osprovit) Coated Total Hip Replacement" (1987).

"ANCA-FIT," brochure. Cremascoli Ortho Group. (undated) 7 sheets.

"BIOLOX® delta, A new ceramic in Orthopaedics," brochure. CeramTec. Printed in Germany (undated) 8 sheets.

"BIOLOX® forte ball heads and cup inserts for hip arthroplasty," brochure. (undated) CeramTec AG Printed in Germany.

"BIOLOX® forte," brochure. CeramTec. Printed in Germany (undated) 53 sheets.

"Book of Abstracts" (May 29-Jun. 1, 2002) Central European Orthopaedic Congress CEOC 4th, Zagreb, Croatia pp. 1-196.

"CERAFIT Composant de frottement alumine-alumine," Revue de Chirurgie Orthopédique et réparatrice de l'appareil moteur, Organe de la Société Française de Chirurgie Orthopédique et Traumatologique, (Sep. 1995) vol. 85 No. 5, Ceraver.

"Comparative Analysis Alumina Ceramic versus Zirconia Ceramic, Alumina Ceramic The Gold Standard for 30 Years," (2002) Wright™.

"DePuy Introduces New Metal Head for Hip." http://www.vpico.comarticlemanager/printerfriendly.aspx?article=235071 (Web accessed Apr. 23, 2009) 1 sheet.

"DePuy Orthopaedics Launches Pinnacle™ Hip Solutions with Trueglide™ Technology," Medical News Today (Mar. 10, 2008) http://www.medicalnewstoday.com/printerfriendlynews.php?newsid=100053 (Web accessed Apr. 23, 2009).

"Dynasty™ Acetabular Cup System," Surgical Technique brochure. (2007) Wright Medical Technology, Inc. 24 sheets.

"FriaTep-Vario-System, nach Prof. Dr. Stock," product brochure/catalog (1989).

"Lineage; Ceramic-on-Ceramic Acetabular Cup System," Surgical Technique brochure, (2003) Wright Medical Technology, Inc. 12 sheets.

McTighe, Timothy, "Cementless Modular Stems," (May 2002) JISRE Update. Joint Implant Surgery & Research Foundation 3 sheets.

"Patient Education: Ceramic-on-Ceramic Hip Replacement—Stryker Brochure, The Trident Ceramic Acetabular System," Connecticut Orthopaedic Specialists. http://www.minottiortho.com/paqes/ceramic_5.php (Web accessed Apr. 23, 2009) 4 sheets.

"PE Wear is the No. 1 Problem of Artificial Hip Joints. The Solution: MonoDome Metal/Metal Articulation," flyer. EMCC Engineering Manufacturing Consulting Corporation AG (SA, Ltd.) 2 sheets (undated).

"Pinnacle Hip Solutions®, Never Stop Moving™," brochure. Design Rationale (2008) DePuy Orthopaedics, Inc. 34 sheets.

"Pinnacle Hip Solutions®, never stop moving™," brochure. DePuy Orthopaedics, Inc. http://www.hipreplacement.com/DePuy/technology/?printerFriendlyTheme=true (Web accessed Apr. 23, 2009) 2 sheets.

"PLASMACUP SC Acetabular Cup," AESCULAP® B.Braun Melsungen AG http://www.bbraun.com/index.cfm?uuid=26EA6AA4838D495B8A895420A83BD099&obj . . . (Web accessed Dec. 5, 2002) 4 sheets.

"Plasmacup® Aesculap Orthopaedics," brochure. Aesculap Implant Systems (Jan. 2008) 16 sheets.

"PLASMACUP® SC," AESCULAP Products—Orthopaedics—Joint Implants, http://www.aesculap.com/e/produkte/ot/gelenk_implantate/plasmacup_sc/otp_ps.htm (Web accessed Aug. 15, 2001).

"PLASMACUP® SC," AESCULAP® Products—Joint Implants. (2001) http://www.aesculap.de/e/produkte/ot/gelenk_implantate/plasmacup_sc/otp_ps.htm (Web accessed Apr. 14, 2003) 2 sheets.

"PROFEMUR R Revision Prosthesis" brochure. Cremascoli Ortho Group (undated) 9 sheets.

"PROFEMUR™ Total Hip System," Surgical Technique brochure. (2002) Wright Medical Technology pp. 1-24.

"Prospective Sales Agent Information," OTI Osteoimplant Technology, Inc. (Nov. 1999-Oct. 2000) 27 pages.

"Prostheses and Instrumentation, The Furlong® H-A.C. Total Hip Replacment," catalog/brochure. (1987) JRI Joint Replacement Instrumentation Ltd. pp. 1-12 of 16 sheets.

"Signature™ Personalized Patient Care, Surgical Technique Addendum to the Vanguard Knee System" brochure. Biomet® Orthopedics, Inc. (2009) pp. 1-8.

"Smith & Nephew launches R3 Acetabular System," press release. http://global.smith-nephew.com/master/news_launch_r3_acetabular_23411.htm (Web accessed Mar. 13, 2008).

"Stanmore Modular Hip System, Timeless Design," brochure. (Sep. 30, 1998) Biomet, Inc. 12 sheets.

"Stryker Trident Hip Implant Component Recall Latest Bad News for Company Since FDA Warning Letter," NewsInferno.com (Jan. 22, 2008) http://www.newsinferno.com/archives/2425 (Web accessed Apr. 23, 2009) 3 sheets.

"The 'triradius' CERAFIT cups: History and concept," CERAVER brochure. http://www.ceraver.fr/anglais/PRODUITS/cotylescerafit-triradius.htm (Web accessed Jan. 24, 2003) 1 sheet.

"The Only Answer: CERAFIT and its Alumina-Alumina Combination," brochure. (Apr. 1995) Ceraver Osteal. 11 sheets.

"Thinking Outside the Cup," Smith & Nephew, Inc. advertisement. (2008) Joint Reconstruction.

"Trident Polyethylene Hip System," 4 individual 1-sheet web pages, Stryker Orthopaedics http://www.stryker.com/jointreplacements/sites/trident/polyj/innerchange.php (Web accessed Jun. 15, 2004) http://www.stryker.com/jointreplacements/sites/trident/healthcare/next5.php (Web accessed Jun. 15, 2004) http://www.france.stryker.com/index/st_pag_medic-home/fr_pag_info-prod/fr_pag_hanche-acetabular-intro/fr_pag_hanche-cup-trident-poly.htm (Web accessed Jun. 15, 2004) http://www.stryker.com/jointreplacements/sites/trident/poly/ (Web accessed Jun. 15, 2004).

"Trilogy® Acetabular System" brochure. Zimmer (2002) 6 sheets.

"What We Led, What We Said, What We Proved," brochure. (2005) Stryker Orthopaedics. 7 sheets.

"Zimmer® Continuum™ Acetabular System," Surgical Technique brochure. (2009) Zimmer, Inc. 25 sheets.

AESCULAP web page depicting "ceramic on ceramic bearing" http://www.aesculap.com/e/produkte/ot/gelenk_implantate/modular_ker/otp_mod.htm (Web accessed Aug. 15, 2001) 1p.

Antonio, James A. et al., "New Experience with Alumina: Alumina Ceramic Bearings for Total Hip Arthroplasty," (2003) Stryker® Howmedica Osteonics 11 sheets.

BF Cup catalog sheet identifying Axis I and Axis II (Jan. 2002) 3 sheets.

Blömer, W., "Design Aspects fo Modular Inlay Fixation." (Mar. 8, 1997) Performance fo the Wear Couple BIOLOX forte in HIP Arthroplasty, Proceedings of the 2nd Symposium on Ceramic Wear Couple, Stuttgart (Germany) pp. 95-104.

Boehler, M., et al. "Migration Measurement of Cementless Acetabular Components: Value fo Clinical and Radiographic Data," Orthopedics, Migration of Acetabular Components (Aug. 1998) vol. 21 No. 8, pp. 897-900.

Bohler, M., et al., "Comparison of Migration in Modular Sockets with Ceramic and Polyethylene Inlays," Orthopedics, Migration in Modular Sockets (Dec. 2000) vol. 23 No. 12, pp. 1261-1266.

Boutin, P., et al., "The use of dense alumina-alumina ceramic combination in total hip replacement," Journal of Biomedical Materials Research (1988) vol. 22 pp. 1203-1232.

Böhler, M., et al., "Ergebnisse mit der Keramik-KeramikGleitpaarung in der Hiiftendoprothetik", (1996) Proceedings des 1. CERASIV-Symposiums am Mar. 23, 1996 in Stuttgart Herausgegeben von Wolfhart Puhl, 64 Abbildungen . 31 Tabellen pp. 34-38.

Ceraver Osteal brochure for the following products: "The Cerafit Cup"; "The Answer: CERAL Al2O3-Al2O3 Combination"; and "The Cerafit Cup." (1993).

Clarke, Ian C., "Role of Ceramic Implants, Design and Clinical Success with Total Hip Prosthetic Ceramic-to-Ceramic Bearings," Clincal Orthopaedics and Related Research™ (Sep. 1992) No. 282 pp. 19-30.

Department of Health & Human Services 510(I) Summary for DePuy. Trade/Device Name: DePuy Pinnacle® Constrained Acetabular Liner. May 18, 2007 (7 pages).

Diehl, K., et al., "Der zementfreie Hüftgelenkersatz bei Hüftkopfnekrosen mit dem MC-Hüftgelenk," (1991) The Stuhler (Ed.) Hüftkopfnekrose, Springer-Verlag Berlin Heidelberg. 3 sheets.

Effenberger, H., "Hüftendoprothetik, Konstruktion, Klassivation, Implantate, Egrebnisse," (2007) pp. 1-15.

Effenberger, H., et al., "Modifikationen von Form, Material und Modularität der Schraubpfannen," Biomedizinische Technik, Band 47 Heft Jun. 2002 pp. 169-175.

Fuchs, G.A., "2-4 Year Clinical Results with a Ceramic-on-Ceramic_Articulation_in_a_New_Modular_THR-System." Bioceramics in Hip Joint Replacement (Feb. 2000) pp. 39-45.

Fuchs, G.A., et al., "First 2-5 years results of single designed cemented and noncemented BF prosthesis in total hip arthroplasty." The Orthopedic Journal of China (Sep. 1999) EDIC China, vol. 6 No. 9 pp. 711-715.

Gekeler, J., "Sphärische Press-fit-Pfannen und erste klinische Erfahrungen mit der Keramik-Gleitpaarung (PLASMACUP SC)." Bioceramics in Orthopaedics—New Applications, Proceedings of the $3^{rd}$ International Symposium on Cerami Wear Couple (Germany) (Feb. 14, 1998) pp. 32-38.

International Search Report and Written Opinon mailed Mar. 16, 2010 for PCT/US2009/065651 claiming benefit of U.S. Appl. No. 12/624,142, filed Nov. 23, 2009.

Radermacher, "Computer Assisted Orthopaedic Surgery with Image Based Individual Templates," Clinical Orthopaedics and Related Research No. 354, pp. 28-38 (1998) Lippincott Williams & Wilkins.

Salzer, M., et al., "A Bioceramic Endoprosthesis for the Replacement of the Proximal Humerus," Archives of Orthopaedic and Traumatic Surgery. (1979) vol. 93 pp. 169-184.

Salzer, M., et al., Keramische Endoprothesen der oberen Extremität, Z. Orthop. (1975) 113 pp. 458-461.

Scheller, G et al. "MPF Modular Press Fit Cup—the Concept, Experience and First Results." *BIOLOX Symposium*. Georg Thieme Verlag, (2000) pp. 35-38.

Sedel, Laurent, M.D., "Evolution of Alumina-on-Alumina Implants," Clinical Orthopaedics and Related Research (2000) No. 379, pp. 48-54.

Sedel, Laurent, M.D., et al., "Alumina-Alumina Hip Replacement in Patients Younger Than 50 Years Old," Clinical Orthopaedics and Related Research (1994) No. 298, pp. 175-183.

Willmann, G., "Modularity—The Chance to Solve the Wear Problems in Total Hip Replacement." *BIOLOX Symposium*. Ferdinand Enke Verlag, (1996) pp. 94-99.

Willmann, G., et al., "Keramische Pfanneneinsätze für Hüftendoprothesen Teil 2: Bauteilprüfung und -sicherheit; Ceramic Acetabular Cups for Total Hip Replacement Part 2: Component Testing and Reliability," Biomedizinische Technik (1996) Band 41 Heft 10 pp. 284-290.

Willmann, G., et al., "Keramische Pfanneneinsätze für Hüftendoprothesen; Ceramic Cup Inserts for Hip Endoprostheses," Biomedizinische Technik (1996) Band 41 Heft 4 pp. 98-105.

International Preliminary Report on Patentability and Written Opinion mailed Jan. 26, 2012 for PCT/US2010/041826 claiming benefit of U.S. Appl. No. 12/502,848, filed Jul. 14, 2009.

* cited by examiner

MULTIPLE BEARING ACETABULAR PROSTHESIS

FIELD

The present disclosure relates to a modular prosthesis, particularly to an acetabular prosthesis including a plurality of liners operable to interconnect with a single acetabular cup.

BACKGROUND

This section provides background information related to the present disclosure which is not necessarily prior art.

Articulating regions of the anatomy can include areas where two bone sections move relative to one another. For example, an acetabulum can provide a region for articulation with a femoral head. The articulating region, however, can become injured or worn, but it can be replaced with various prostheses. Such prostheses can replace the acetabulum, the femoral head, and various other portions of the femur, or other combinations thereof. The replacement of both the acetabulum and the femoral head is generally referred to as a total joint replacement.

The total joint replacement of the acetabulum and the femoral head can require a bearing or articulating surface for both the femoral head and the acetabulum. The articulating surfaces are generally positioned relative to the various portions of the remaining natural anatomy in a substantially fixed manner. Materials must be selected for the bearing surfaces for various purposes.

SUMMARY

This section provides a general summary of the disclosure, and is not a comprehensive disclosure of its full scope or all of its features.

An acetabular prosthesis assembly can include an acetabular cup and a first liner. The acetabular cup can have an outer surface, an inner surface and an upper rim extending between the outer surface and the inner surface. The acetabular cup can have a cup connection portion including a groove formed on an upper face of the upper rim. The first liner can have an outer cup engaging surface and a liner connection portion that extends from a flange of the first liner. The liner connection portion can have a finger that is received by the groove formed on the upper face of the acetabular cup that selectively couples the liner connection portion with the cup connection portion in an assembled position.

According to additional features, the cup connection portion can be collectively formed by an inner wall and an outer wall that are offset by the groove. The groove can extend annularly around the upper rim. One of the inner and outer walls can include an undercut formed in the groove. The first liner can include a protrusion extending from the finger that nests in the undercut of the acetabular cup in the assembled position.

According to still other features, the acetabular cup can further include an anti-rotation counterbore defined by the inner liner engaging surface. The first liner can include an anti-rotation projection extending from the outer cup engaging surface that cooperatively locates at the anti-rotation counterbore of the acetabular cup in the assembled position.

According to additional features, the cup connection portion can further comprise a plurality of grooves formed radially on the upper face of the upper rim. The liner connection portion can further comprise a plurality of radial flanges each having a finger that selectively mates with selected grooves of the cup connection portion in an assembled position. Each of the fingers can have oppositely extending protrusion portions that selectively locate within opposing cut-out portions formed on the upper rim at the plurality of grooves.

According to yet other features, the first liner can be formed of polyethylene. The acetabular prosthesis assembly can additionally comprise a second liner and a third liner. The second liner can be formed of cobalt-chromium. The second liner can have a male taper portion that selectively engages a complementary female taper portion formed on the inner liner engaging surface of the acetabular cup in an assembled position. The third liner can be formed of ceramic. The third liner can have a male tapered portion that selectively engages the female tapered portion on the inner liner engaging surface of the acetabular cup in an assembled position. The acetabular cup can selectively and alternatively mate with any of the first, second or third liners.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
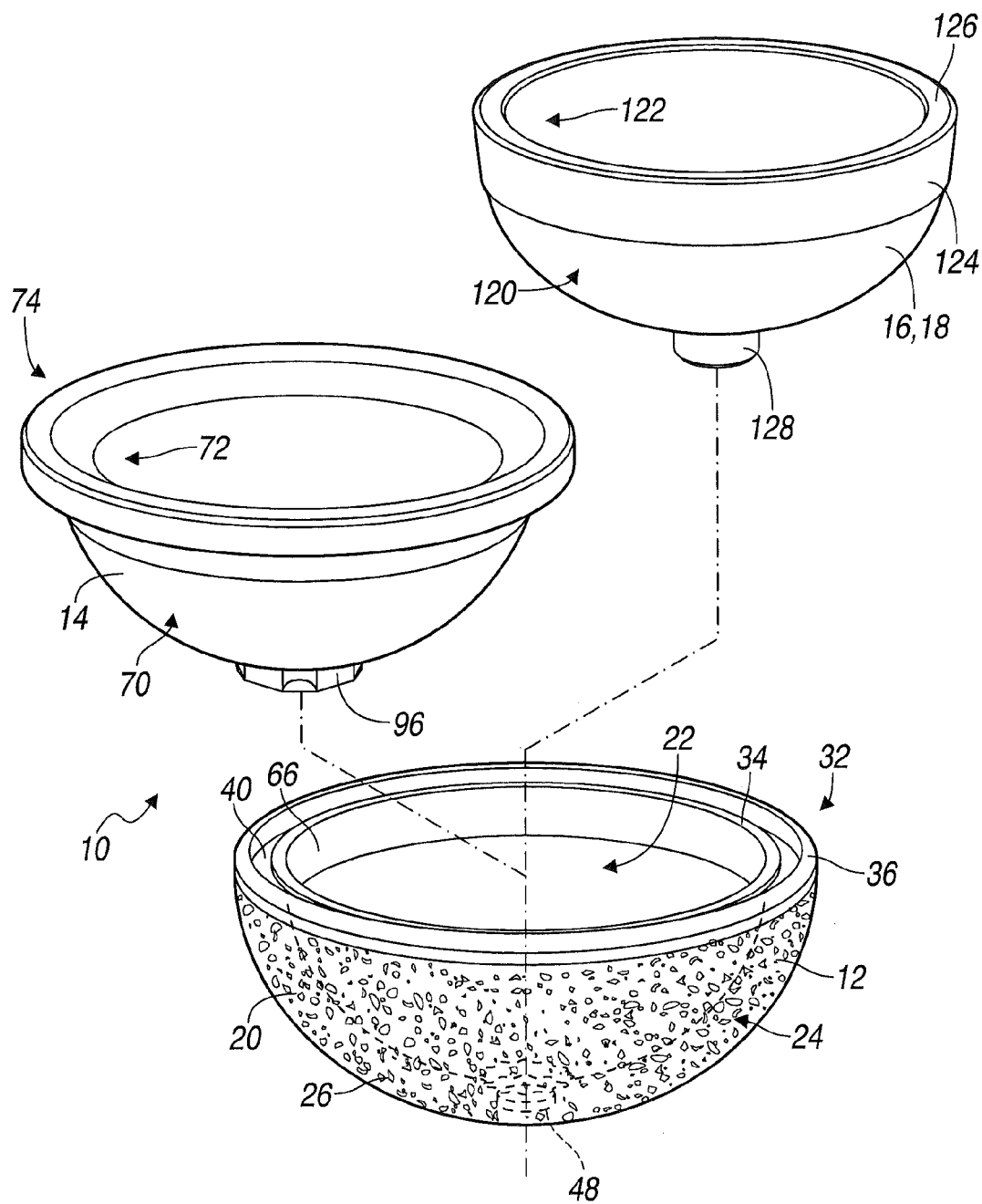
FIG. 1 is a perspective exploded view of an acetabular prosthesis assembly constructed in accordance to one example of the present teachings.

With initial reference to FIG. 1, an acetabular prosthesis assembly constructed in accordance to one example of the present teachings is shown and generally identified at reference numeral 10. The acetabular prosthesis assembly 10 can generally include a single acetabular cup 12 that can be selectively and alternatively interconnected with a first bearing or liner 14, a second bearing or liner 16 or a third bearing or liner 18. According to one example, the first liner 14 can be formed of any appropriate materials, such as polymers including ultra-high molecular weight polyethylene (UHMWPE) or polyetheretherketone (PEEK). The second liner 16 can be formed of a substantially or relatively hard or rigid material, such as metals (e.g., titanium, titanium alloys, stainless steel alloys, cobalt chromium alloys). The third liner 18 can be formed of a substantially or relatively hard or rigid material, such as a ceramic material. In one example, the second and third liners 16 and 18 can have an equivalent geometry. As such, the second and third liners 16 and 18 have been denoted in the drawings simply as a single liner.

Briefly, the provision of the first, second and third liners 14, 16 and 18 allow for a pre-operative or intra-operative selection of liners for positioning within the acetabular cup 12. In addition or alternatively, the provision of the first, second and third liners 14, 16 and 18 that can each engage a common acetabular cup 12 can minimize the number of parts for a procedure. For example, rather than requiring a first acetabular cup to engage the first liner 14 and a second acetabular cup to engage the second liner 16 and/or a third acetabular cup to engage the third liner 18, only the single acetabular cup 12 is needed to engage all of the first, second and third liners 14, 16 and 18. As will be described, the first liner 14 can include different connection portions relative to the second and third liners 16 and 18 for interconnecting with the single acetabular cup 12.

Figure 2:
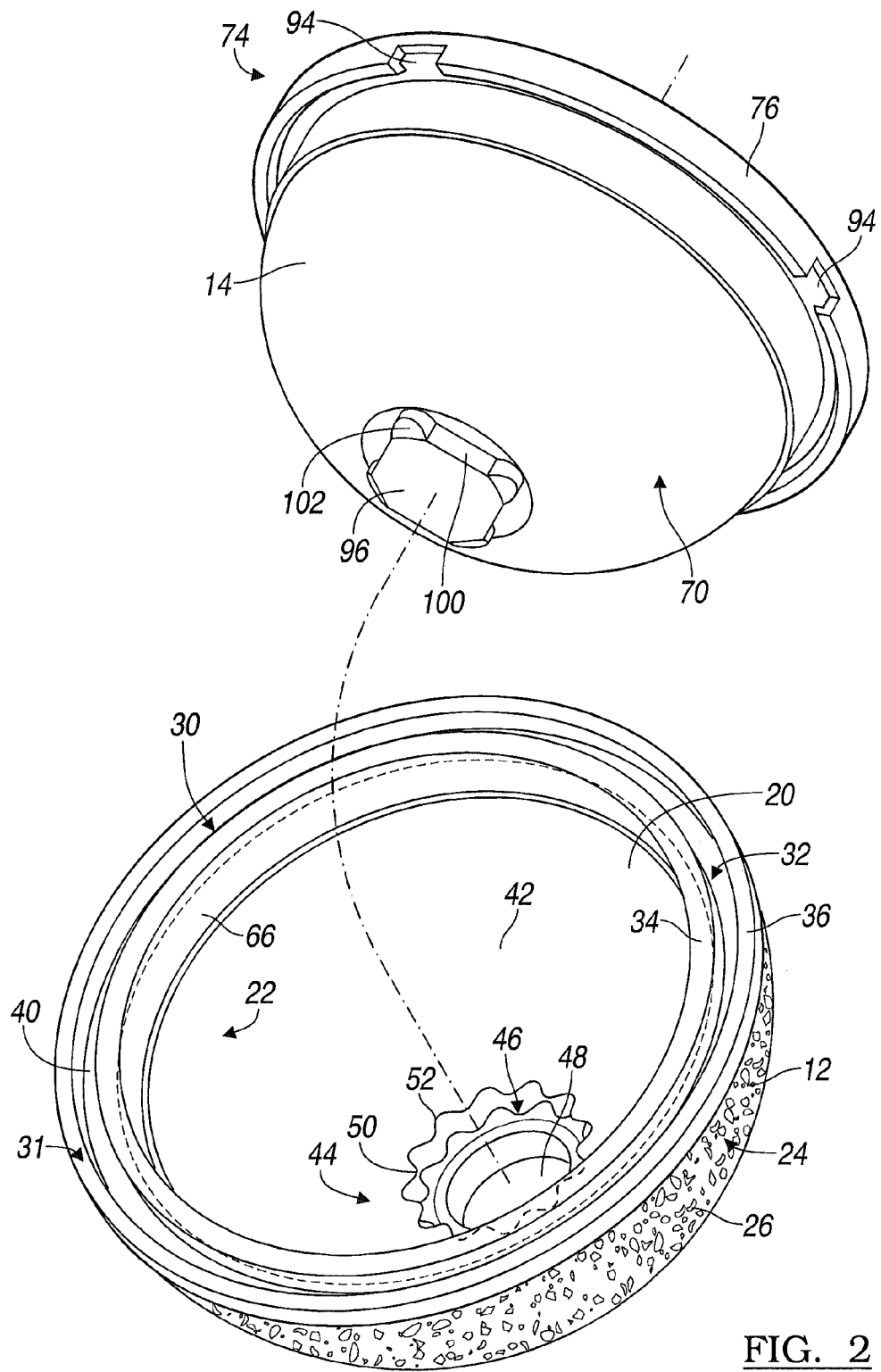
FIG. 2 is a perspective exploded view of an acetabular cup and first liner of the acetabular prosthesis assembly of FIG. 1.

With continued reference to FIG. 1 and additional reference now to FIGS. 2 and 3, the acetabular cup 12 will be described in greater detail. According to one example, the acetabular cup 12 can be formed of biocompatible metallic material, such as, but not limited to titanium, titanium alloy, stainless steel alloy and cobalt-chromium alloy. The acetabular cup 12 can generally include a hemispherical body 20 having an inner liner engaging surface 22 and an outer bone engaging surface 24. The outer bone engaging surface 24 can have a porous metal coating 26. The acetabular cup 12 can include an upper rim 30 that extends between the inner liner engaging surface 22 and the outer bone engaging surface 24. The upper rim 30 can include an upper face 31 having a cup connection portion 32. The cup connection portion 32 can collectively be formed by an inner wall 34 and an outer wall 36 offset by an annular groove 40 formed around the upper rim 30 where the cup connection portion 32 is outside of the inner liner engaging surface 22. A portion of the inner wall 34 can be common with the inner liner engaging surface 22. A portion of the outer wall 36 can be common to the outer bone engaging surface 24. The inner liner engaging surface 22 of the acetabular cup 12 can define a cup cavity 42. As best illustrated in FIG. 2, the cup connection portion 32 is outside of the cup cavity 42. The inner end outer walls 34 and 36 can be parallel to an axis through an apex of the acetabular cup 12.

The acetabular cup 12 can include an apical portion 44 that includes an anti-rotation counterbore 46 formed thereat. The anti-rotation counterbore 46 is defined in the inner liner engaging surface 22. The anti-rotation counterbore 46 can include a bore or apical hole 48 that passes entirely through the acetabular cup 12. The anti-rotation counterbore 46 includes a series of inset and outset portions 50 and 52 formed therearound.

The cup connection portion 32 will now be described in greater detail. The cup connection portion 32 can include an undercut 56 (FIG. 3) formed from the annular groove 40 into the inner wall 34. In one example, the undercut 56 can extend radially into the inner wall 34 in a direction opposite of the outer wall 36. The inner wall 34 can include a lip surface 58. In one example, an upper surface of the inner wall 34 can define a first plane 60 and an upper surface of the outer wall 36 can define a second plane 62. The first and second planes 60 and 62 can be offset relative to each other. A portion of the inner liner engaging surface 22 proximate to the upper rim 30 can include a female taper 66.

Figure 1A:
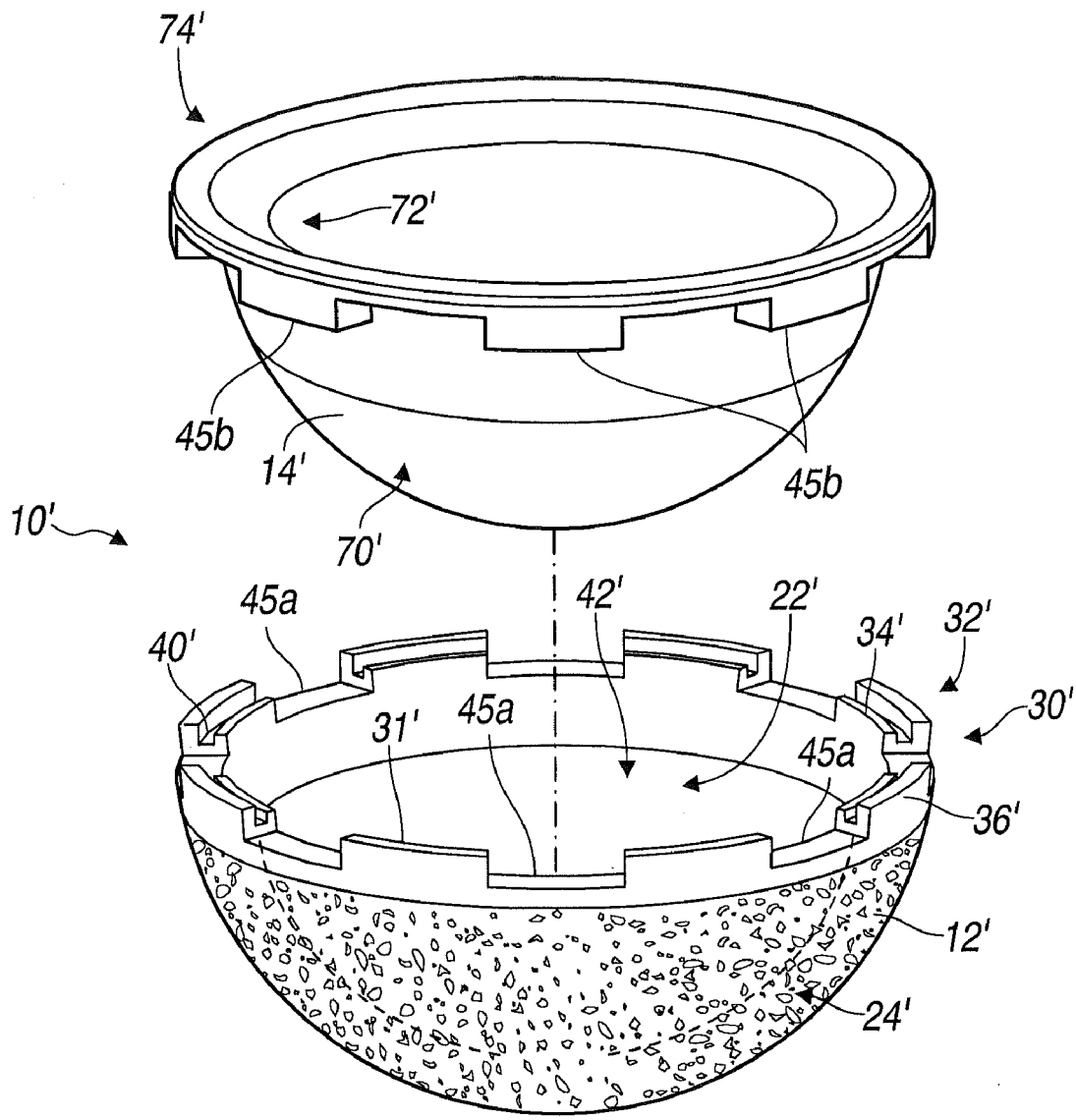
FIG. 1A is a perspective exploded view of an acetabular prosthesis assembly according to additional features.

According to additional features shown in FIG. 1A, an acetabular cup 12' can include an upper rim 30' that extends between the inner liner engaging surface 22' and the outer bone engaging surface 24'. The upper rim 30' can include an upper face 31' having a cup connection portion 32'. The cup connection portion 32' can collectively be formed by an inner wall 34' and an outer wall 36' offset by an annular groove 40' formed around the upper rim 30' where the cup connection portion 32' is outside of the inner liner engaging surface 22'. A portion of the inner wall 34' can be common with the inner liner engaging surface 22'. A portion of the outer wall 36' can be common to the outer bone engaging surface 24'. The inner liner engaging surface 22' of the acetabular cup 12' can define a cup cavity 42'. A series of inset portions 45a can be provided around the rim 30' configured to cooperatively receive a complementary series of outset portions 45b provided on liner 14'. Unless otherwise described, the acetabular cup 12' and liner 14' can be configured similar to the acetabular cup 12 and liner 14. Like features have been identified with a common reference numeral having a "prime" suffix.

Figure 3:
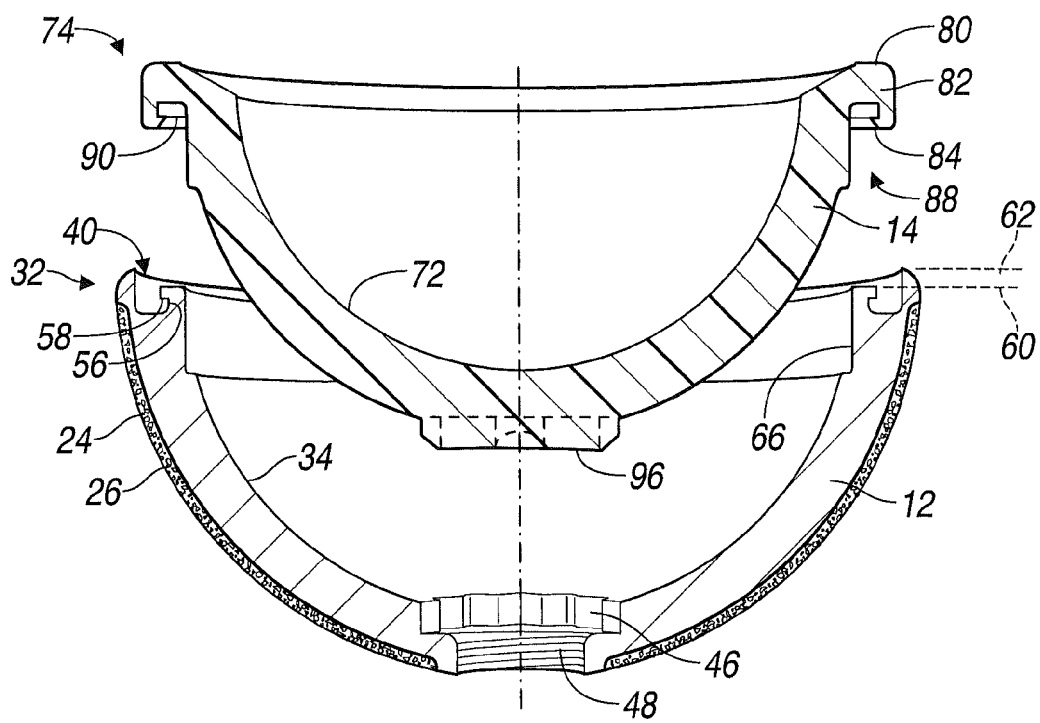
FIG. 3 is a cross-sectional exploded view of the acetabular cup and first liner of FIG. 1.
Figure 4:
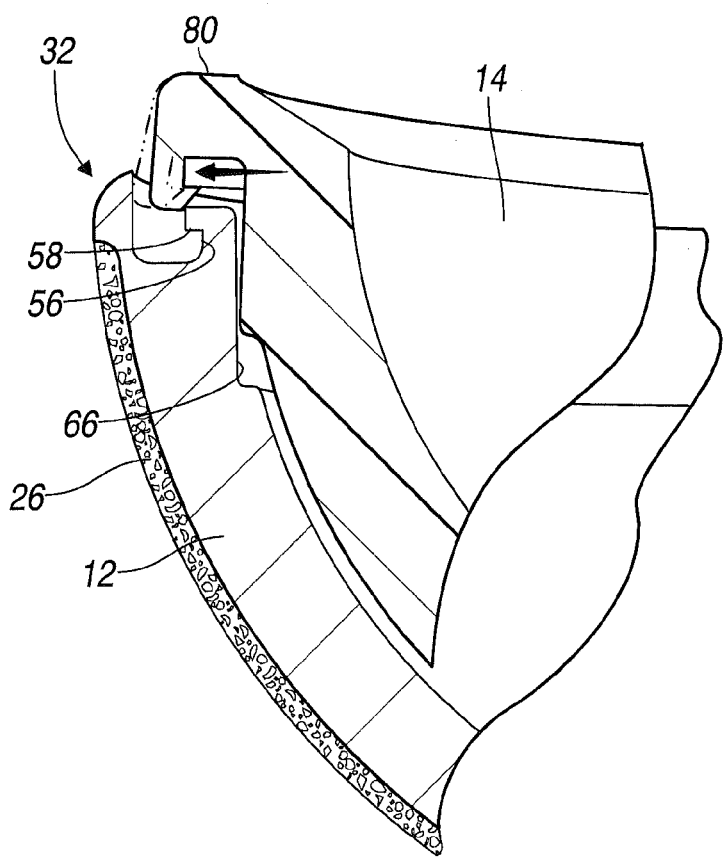
FIGS. 4-6 are partial cross-sectional views of the acetabular cup and first liner of FIG. 1 shown during an exemplary assembly sequence.
Figure 22:
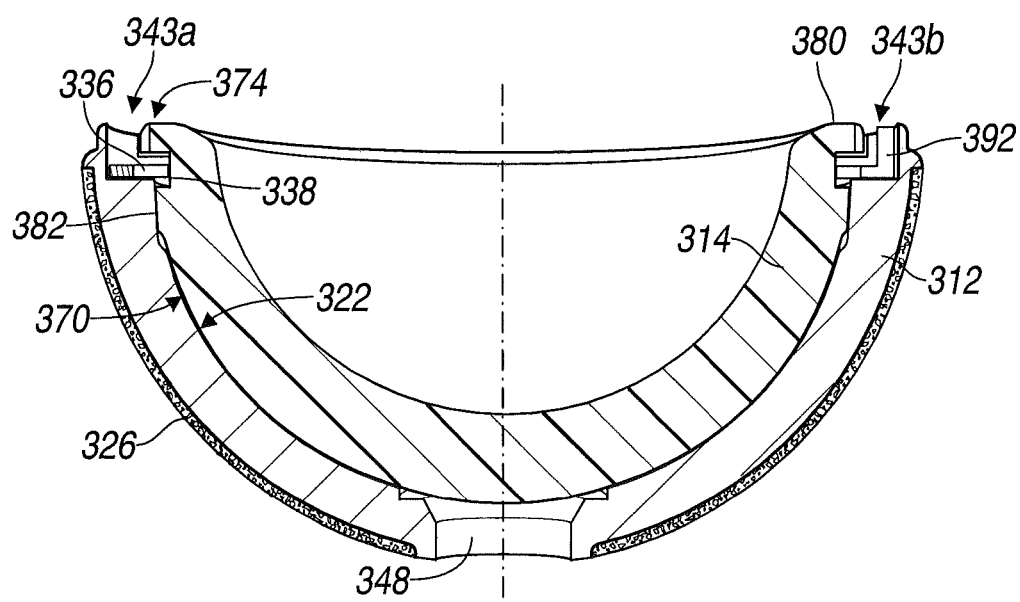
FIG. 22 is a cross-sectional view of the assembled acetabular cup, connecting member and first liner taken along line 22-22 of FIG. 21.
Figure 23:
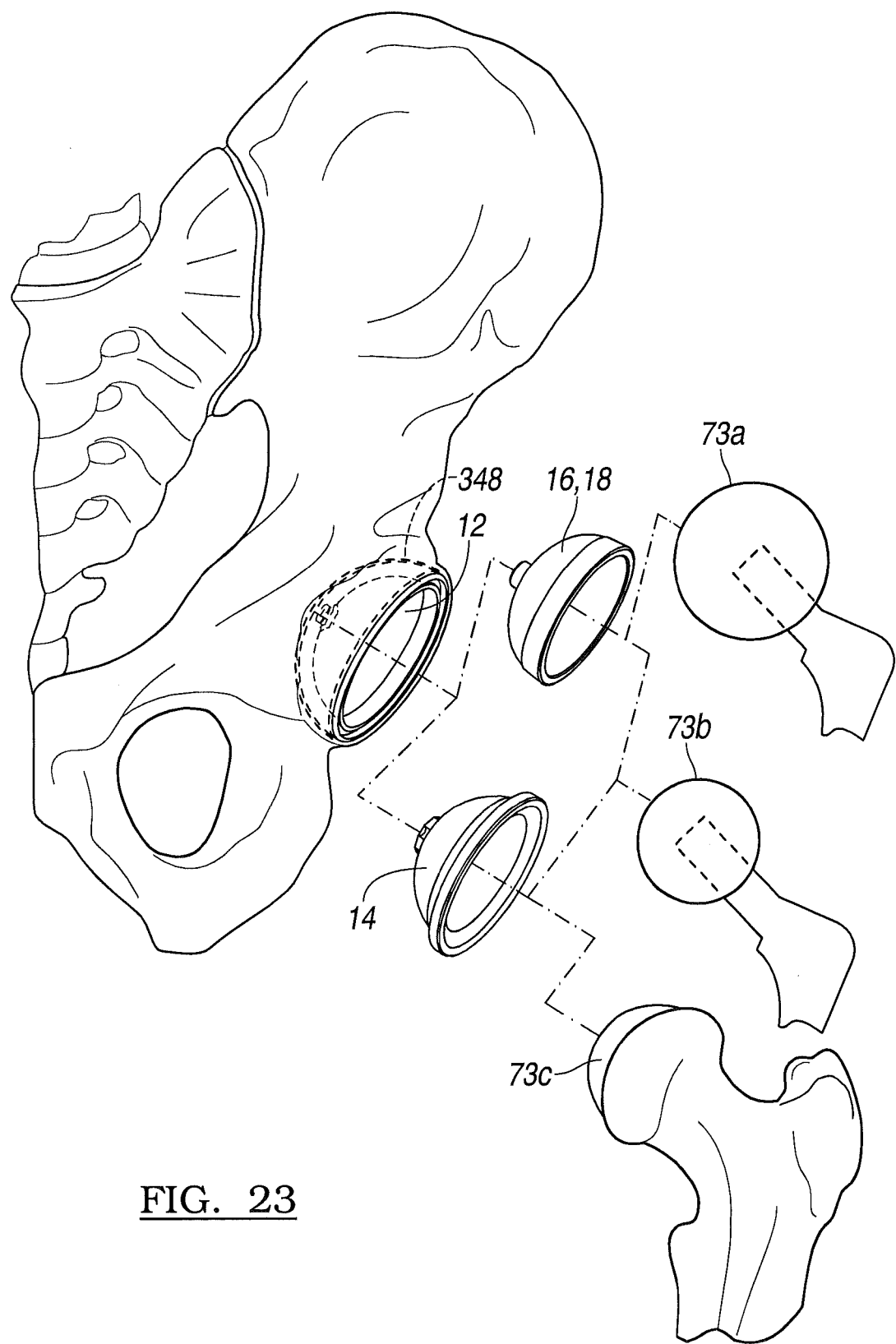
FIG. 23 is an environmental view of an acetabular prosthesis assembly positioned relative to an acetabulum of a patient.

With reference now to FIGS. 2 and 3, the first liner 14 according to one example will be described in greater detail. The first liner 14 can include an outer cup engaging surface 70 and an articulation or internal surface 72 for articulation relative to a femoral implant 73a, 73b (FIG. 22) or a natural femoral head 73c (FIG. 22). The outer cup engaging surface 70 of the first liner 14 can also engage the inner liner engaging surface 22 of the acetabular cup 12 in an appropriate manner, such as a substantially fixed or non-moving manner. The first liner 14 can include a liner connection portion 74 around an upper rim 76. The liner connection portion 74 can include a flange 80 formed around the upper rim 76. The flange 80 can include an annular finger 82 including an annular protrusion 84 that extends in a direction generally toward the outer cup engaging surface 70 of the first liner 14. An annular channel 88 is formed on the first liner 14 generally between the flange 80, finger 82, annular protrusion 84 and the outer cup engaging surface 70. A ridge surface 90 can be provided around the annular protrusion 84. A plurality of relief notches 94 can be formed around the liner connection portion 74 of the first liner 14.

Returning to FIG. 1A, the liner 14' can have an outer cup engaging surface 70', an internal surface 72' and a liner connection portion 74'. As described above, the inset portions 45a of the acetabular cup 12', can cooperatively receive the outset portions 45b of the liner 14'. The alternating inset and outset configuration can act as an anti-rotation feature. Unless otherwise described, the cup connection portion 32' can cooperate with the liner connection portion 74' similar to the cup connection portion 32 and liner connection portion 74.

The first liner 14 can also include an anti-rotation projection 96 extending from an apex of the first liner 14 at the outer cup engaging surface 70. The anti-rotation projection 96 can include an alternating plurality of inset and, outset portions 100 and 102, respectively.

Briefly, the acetabular cup 12 can be implanted into an acetabulum 106 (FIG. 22). In one example, the apical hole 48 can be used with an implantation tool to assist in positioning the acetabular cup 12 in a selected location. Also, an apical plug or other member can be positioned in the apical hole 48, if selected. The acetabular cup 12, according to various embodiments, can also include other bores, external projections, etc., to assist in positioning and fixing the acetabular cup 12 to the anatomy. Exemplary implantation tool systems include apical hole inserters, sold by Biomet Manufacturing Corp. of Warsaw, Ind., USA. As can be appreciated, the acetabular cup 12 can also be provided in different sizes or configurations. For example, a diameter or height of the acetabular cup 12 can be altered based upon different portions that articulate with the first liner 14, the size of the patient, or other appropriate considerations.

With reference now to FIGS. 3-8, assembly of the first liner 14 to the acetabular cup 12 according to one example will now be described. At the outset, a surgeon can align the anti-rotation projection 96 of the first liner 14 with the anti-rotation counterbore 46 of the acetabular cup 12. The inset and outset portions 100 and 102 of the anti-rotation projection 96 can cooperatively nest within complementary inset and outset portions 50 and 52 provided by the anti-rotation counterbore 46. As can be appreciated, the anti-rotation projection 96 does not necessarily need to be confined to one orientation relative to its axis. Rather, the anti-rotation projection 96 can index between a plurality of available rotational positions within the anti-rotation counterbore 46.

Figure 5:
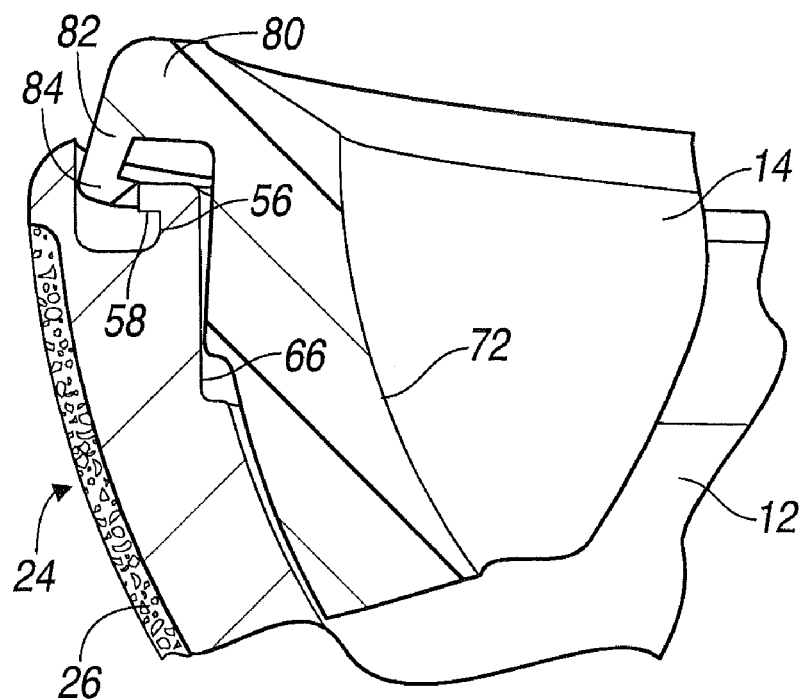

As the surgeon advances the first liner 14 into the cup cavity 42 of the acetabular cup 12, the liner connection portion 74 is directed into engagement with the cup connection portion 32. More specifically, the finger 82 and annular protrusion 84 extending from the flange 80 of the first liner 14 is inserted into the annular groove 40 formed around the upper rim 30 of the acetabular cup 12. During advancement into the annular groove 40, the finger 82 and annular protrusion 84 of the first liner 14 flexes radially outwardly (FIG. 5) away from the inner wall 34 of the acetabular cup 12 until the annular protrusion 84 can retract (FIG. 6) into the undercut 56 of the acetabular cup 12. In one example, the relief notches 94 (FIG. 2) can facilitate outward flexing of the finger 82 and the annular protrusion 84. In the assembled position (FIG. 6), the annular protrusion 84 of the first liner 14 is nestingly received into the undercut 56 of the acetabular cup 12, such that the ridge surface 90 of the first liner 14 opposes the lip surface 58 (as best shown in FIG. 5) of the acetabular cup 12. The attachment is achieved outside of the cavity 42 with the annular protrusion 84 and annular groove 40.

Figure 6:
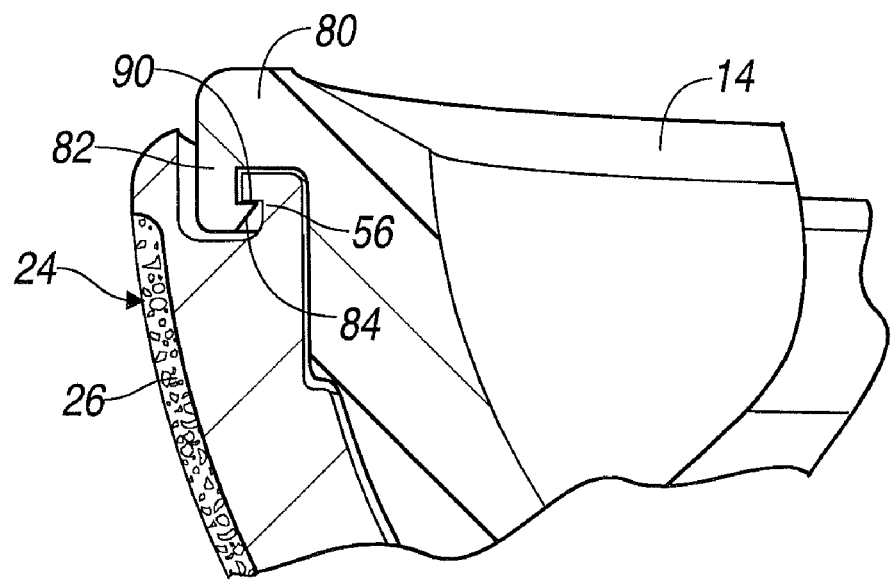
Figure 6A:
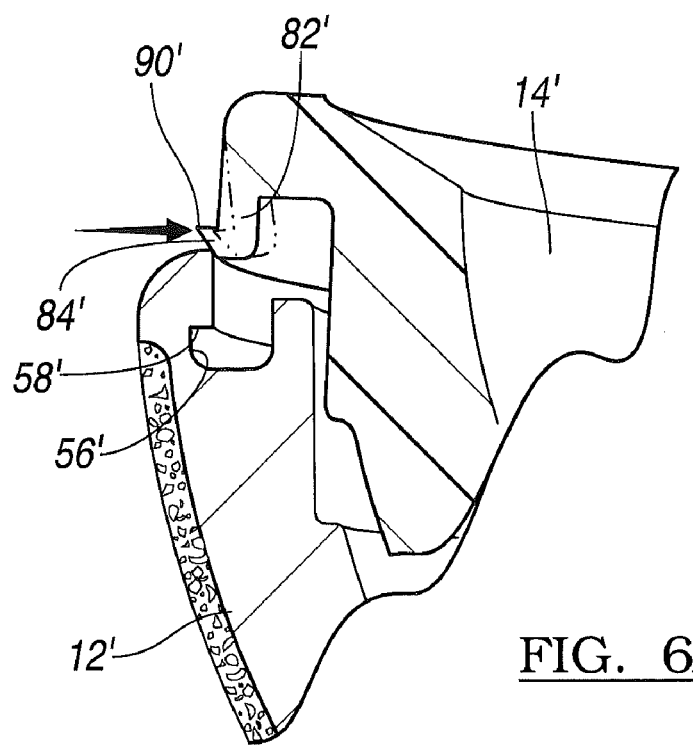
FIG. 6A is a partial cross-sectional view of an acetabular cup and liner according to additional features.
Figure 7:
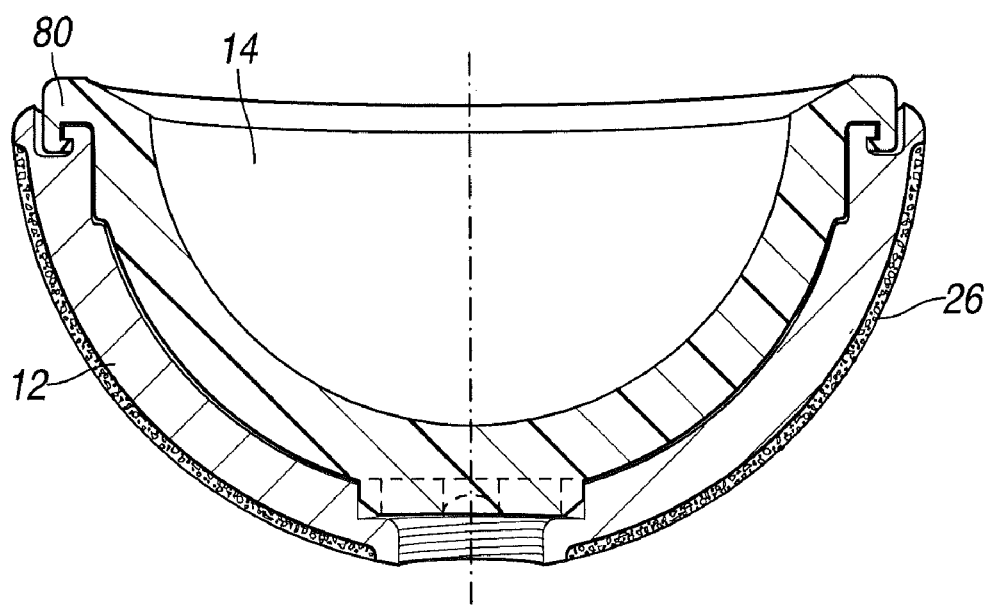
FIG. 7 is a cross-sectional view of the acetabular cup and first liner of FIG. 1 shown in an assembled position.
Figure 8:
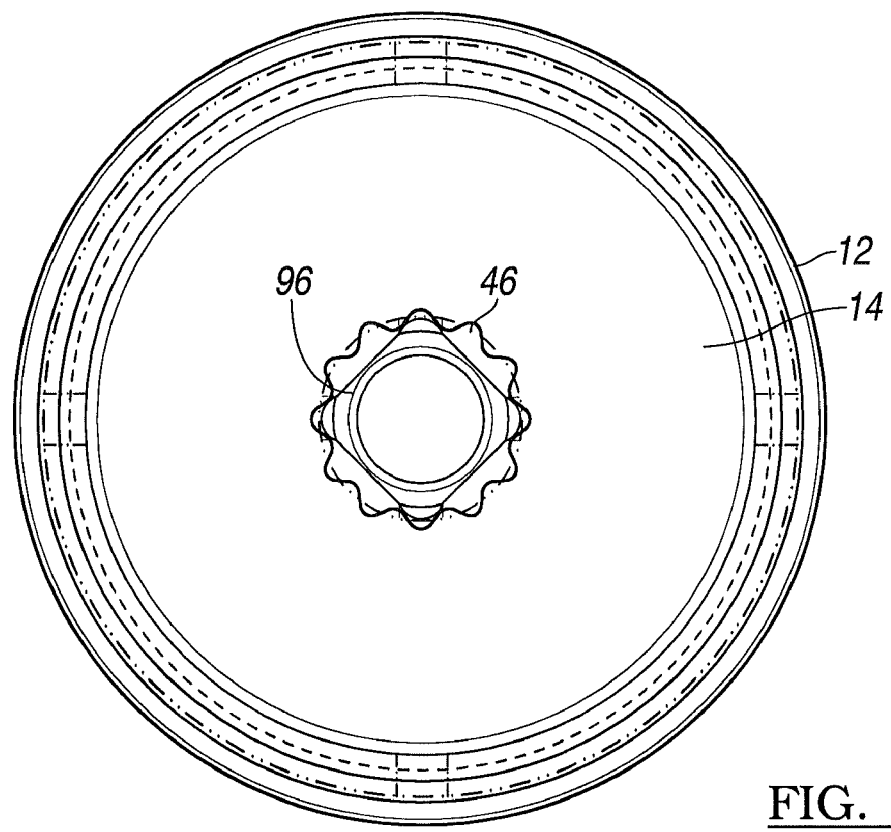
FIG. 8 is a plan view of the assembled acetabular cup and first liner of FIG. 7.

In another example shown in FIG. 6A, a finger 82' has an outwardly facing annular protrusion 84' that flexes inwardly until retracting into an outwardly directed undercut 56'. A ridge surface 90' opposes lip surface 58' when assembled. Like features with the configuration shown in FIG. 6 have been identified with a common reference numeral having a "prime" suffix.

Figure 9:
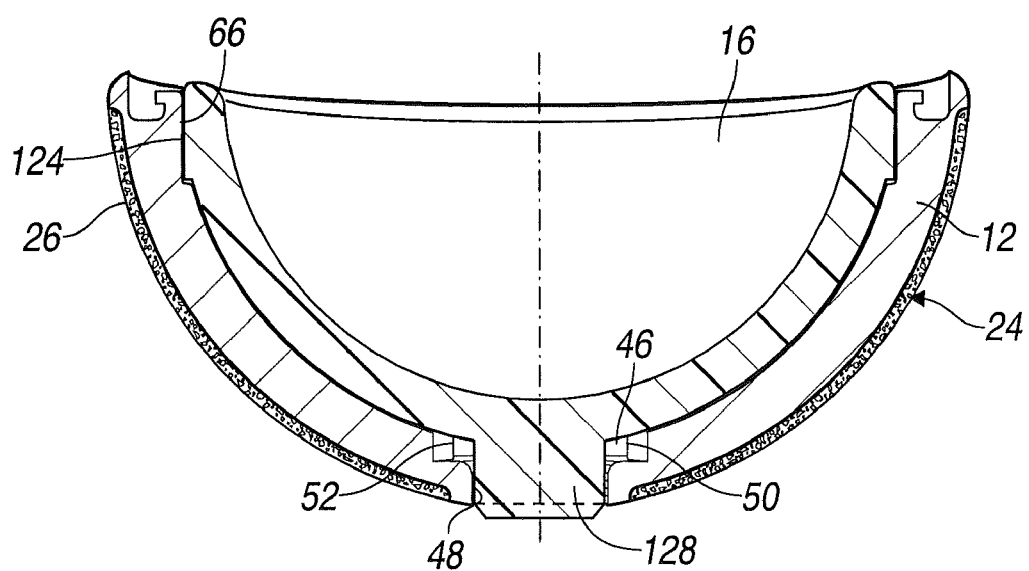
FIG. 9 is a cross-sectional assembled view of the acetabular cup and second liner of FIG. 1.

With reference to FIGS. 1 and 9, the second liner 16 will now be described in greater detail. For discussion purposes, only description of the second (metal) liner 16 will be described. However, it is appreciated that the third (ceramic) liner 18 can be similarly constructed. The second liner 16 can generally include an outer cup engaging surface 120 and an internal articulating surface 122. A male taper 124 can be formed around the outer cup engaging surface 120 near an upper rim 126 of the second liner 16. A projection 128 can extend proud from an apex of the second liner 16 on the outer cup engaging surface 120. The male taper 124 can include any appropriate angle relative to a central or concentric axis of the second liner 16. The angle of the male taper 124 can be substantially identical or similar to an angle provided by the female taper 66 of the acetabular cup 12. The tapers 124 and 66 can include selected angles, such as about 1° to about 45°. The angles can allow the male taper 124 to engage the female taper 66 in a substantially locked or connected manner, such as with a Morse taper. The interconnection of the tapers 124 and 66 can allow a fixation of the second liner 16 into the cup cavity 42 of the acetabular cup 12 at a selected time. The female taper 66 can also assist in aligning the second liner 16 during implantation of the second liner 16 into the acetabular cup 12. As shown in FIGS. 3 and 9, the interconnection of the tapers 124 and 66 occurs below the plane 60 and inward of the female taper 66.

During assembly of the second liner 16 with the acetabular cup 12, a surgeon can generally align the projection 128 of the second liner 16 into the apical hole 48 of the acetabular cup 12. As can be appreciated, an outer wall surface formed by the projection 128 can be offset radially inwardly relative to the inset and outset portions 50 and 52 of the anti-rotation counterbore 46 provided in the acetabular cup 12 (see FIG. 9).

Turning now to FIGS. 10-15, an acetabular prosthesis assembly constructed in accordance to another example of the present teachings is shown and generally identified at reference numeral 210. The acetabular prosthesis assembly 210 can generally include a single acetabular cup 212 that can be selectively and alternatively interconnected with a first bearing or liner 214, a second bearing or liner 216 or a third bearing or liner 218. In one example, the first liner 214 can be formed of any appropriate material, such as polymers including UHMWPE or PEEK. The second liner 216 can be formed of a substantially or relatively hard or rigid material, such as a metal material described above with respect to the second liner 16. The third liner 218 can be formed of a substantially or relative hard or rigid material, such as a ceramic material. In one example, the second and third liners 216 and 218 can have an equivalent geometry. As such, the second and third liners 216 and 218 have been denoted in the drawings simply as a single liner. As with the acetabular prosthesis assembly 10 described above, the acetabular prosthesis assembly 210 allows for pre-operative or intraoperative selection of various liners for alternatively positioning within the acetabular cup 212. In this way, the first, second and third liners 214, 216 and 218 can each engage a common acetabular cup 212 therefore minimizing the number of required components for a procedure.

With continued reference to FIGS. 10-14, the acetabular cup 212 will be described in greater detail. The acetabular cup 212 can be formed of biocompatible metallic material, such as described above with respect to the acetabular cup 12. The acetabular cup 212 can generally include a hemispherical body 220 having an inner liner engaging surface 222 and an outer bone engaging surface 224. The outer bone engaging surface 224 can have a porous metal coating 226. The acetabular cup 212 can include an upper rim 230 that extends between the inner liner engaging surface 222 and the outer bone engaging surface 224. The upper rim 230 can have an upper face 231 including a cup connection portion 232. The cup connection portion 232 can include a plurality of grooves 238 formed in a radial direction into the upper face 231 of the upper rim 230. The upper rim 230 can also include a corresponding series of converging ramp surfaces 239 (FIG. 13) and cut-out portions 240 that collectively make up each of the grooves 238. The inner liner engaging surface 222 of the acetabular cup 212 can define a cup cavity 242 (FIG. 10) that extends below a plane 243 (FIG. 15) that is below the cup connection portion 232. The acetabular cup 212 can include an apical portion 244 having an apical hole 248 that passes entirely through the acetabular cup 212.

The first liner 214 according to one example will be described in greater detail. The first liner 214 can include an outer cup engaging surface 270 and an articulation or internal surface 272 for articulation relative to a femoral implant or a natural femoral head. The outer cup engaging surface 270 of the first liner 214 can also engage the inner liner engaging surface 222 of the acetabular cup 212 in an appropriate manner, such as a substantially fixed or non-moving manner. The first liner 214 can include a liner connection portion 274 around an upper rim 276. The liner connection portion 274 can include a plurality of radial flanges 280 each having a finger 282. A distal end of each finger 282 can include oppositely extending protrusion portions 284.

Figure 11:
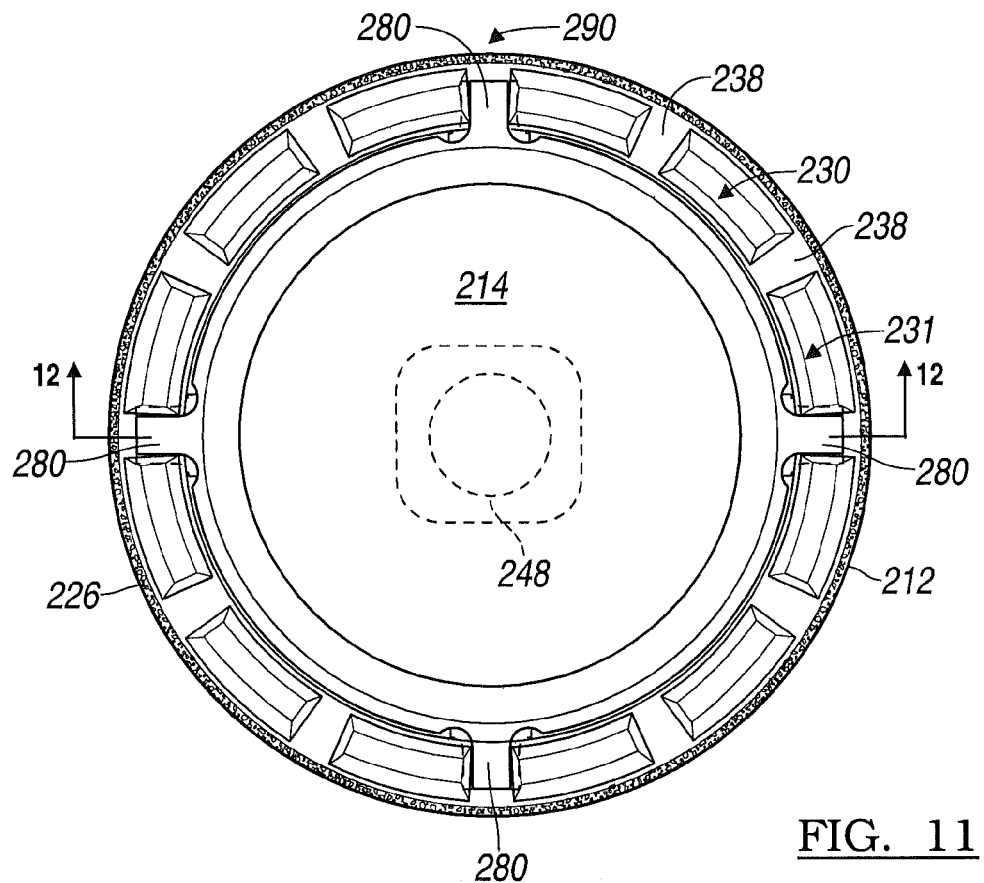
FIG. 11 is a plan view of the acetabular cup and first liner of FIG. 10 shown in an assembled position.
Figure 12:
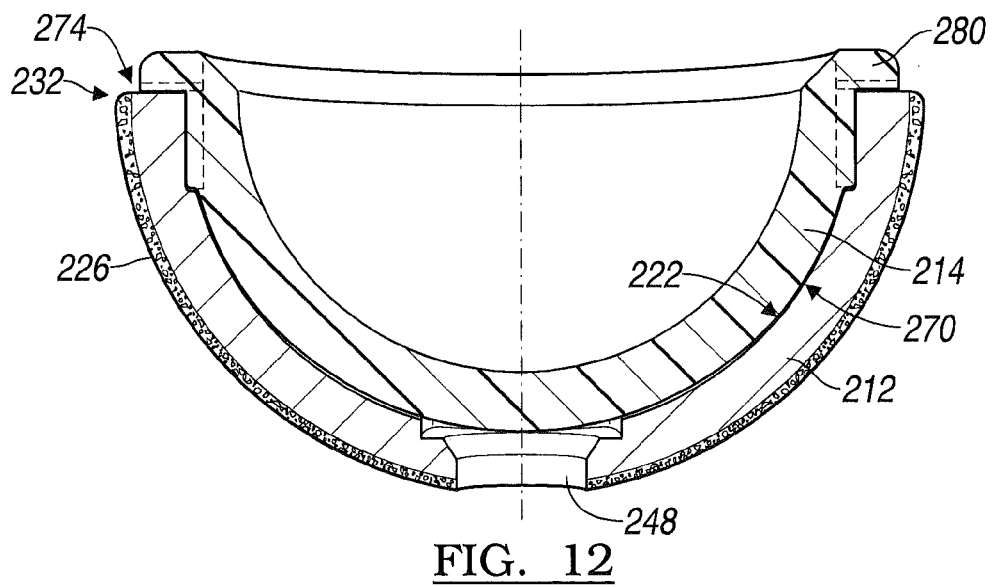
FIG. 12 is a cross-sectional view of the acetabular cup and first liner taken along line 12-12 of FIG. 11.
Figure 13:
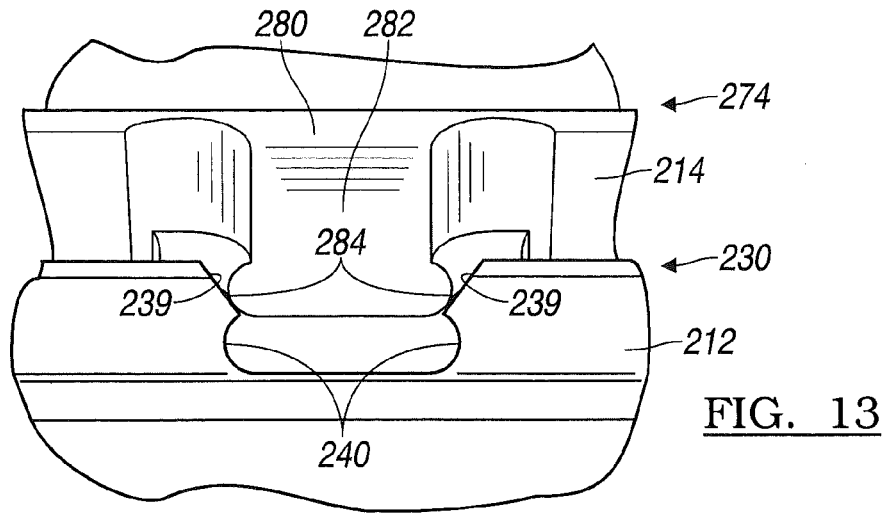
FIGS. 13 and 14 are partial detail views of the acetabular cup and first liner of FIG. 10 shown during an exemplary assembly sequence.
Figure 14:
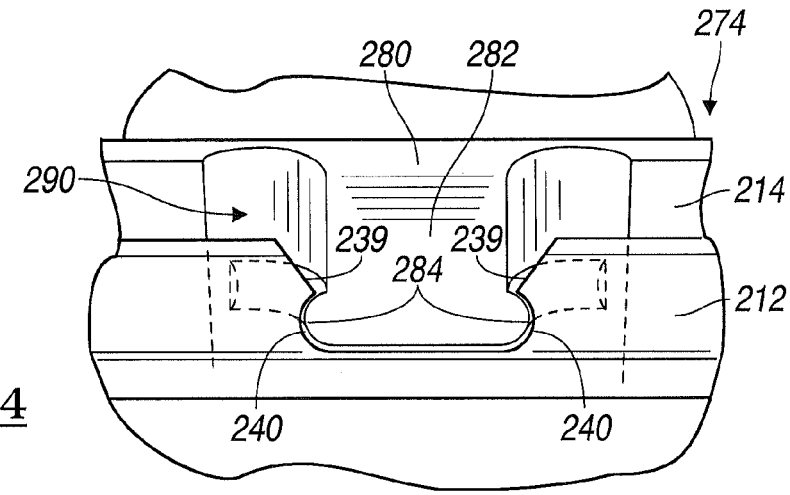

The acetabular cup 212 can be implanted into an acetabulum, such as described above with respect to the acetabular cup 12. Assembly of the first liner 214 to the acetabular cup 212 according to one example will now be described. At the outset, a surgeon can align flanges 280 of the liner connection portion 274 with complementary grooves 238 of the cup connection portion 232 at an area generally outside of the cup cavity 242 and provided on the upper face 231 of the acetabular cup 212. As can be appreciated, the first liner 214 can assume a number of radial locations around its longitudinal axis whereupon the flanges 280 are aligned for receipt into any complementary series of grooves 238. While the exemplary first liner 214 illustrates four flanges 280 and the acetabular cup 12 provides twelve grooves 238, the actual number of the flanges 280 and the grooves 238 is merely exemplary and other combinations may be implemented. Once the respective flanges 280 are aligned for receipt into identified grooves 238 (FIG. 13), the first liner 214 can be further advanced into the cup cavity 242. In one example, the protrusion portions 284 of the flanges 280 can ride along respective ramp surfaces 239 to further guide the respective fingers 282 into the grooves 238. During advancement into the respective grooves 238, the protrusion portions 284 can flex radially inwardly toward each other until the protrusion portions 284 can retract (FIG. 14) into the cutout portions 240 of the grooves 238. In the assembled position, the fingers 282 are confined for rotational movement around the upper rim 230 of the acetabular cup 212 by the respective grooves 238. Therefore, the interaction between the fingers 282 and the grooves 238 can provide an anti-rotation feature 290 (FIG. 11).

Figure 10:
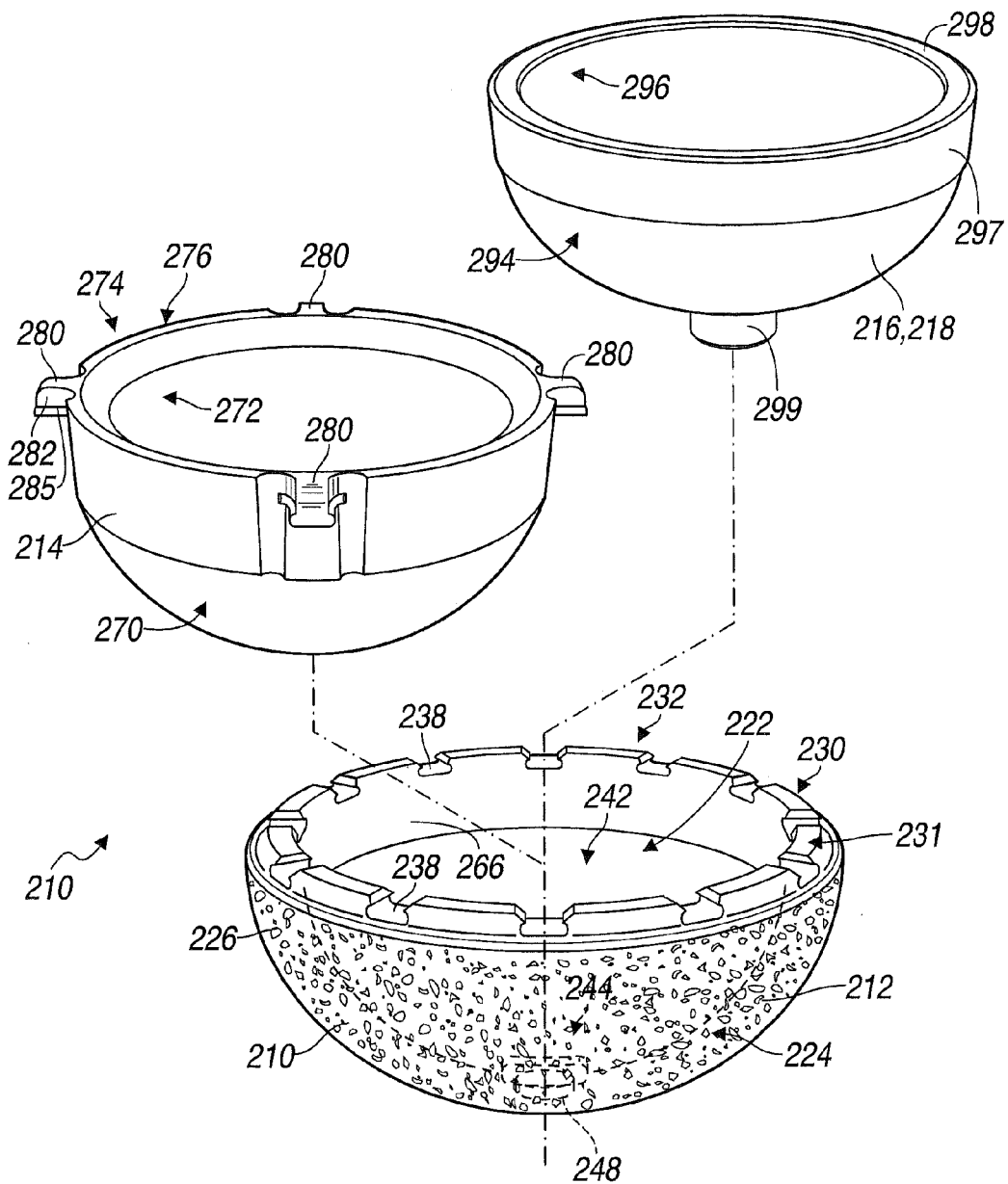
FIG. 10 is a perspective exploded view of an acetabular prosthesis assembly according to another example of the present teachings.
Figure 15:
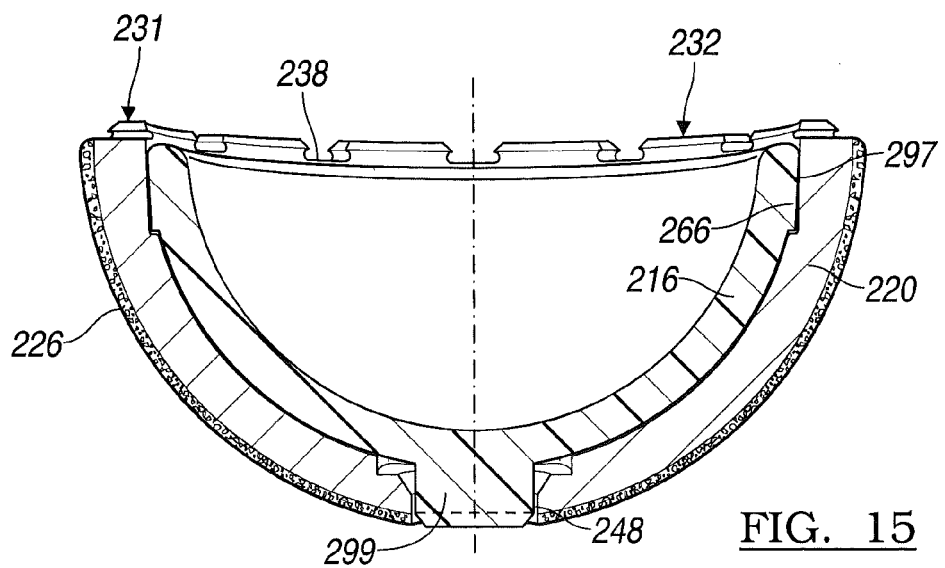
FIG. 15 is a cross-sectional view of the acetabular cup and second liner of FIG. 10 shown in an assembled position.

With reference to FIGS. 10 and 15, the second liner 216 and third liner 218 can be constructed similarly to the second and third liners 16 and 18 described above. The second liner 216 can generally include an outer cup engaging surface 294 and an internal articulating surface 296. A male taper 297 can be formed near an upper rim 298 of the second liner 216. A projection 299 can extend proud from an apex of the second liner 216 on the outer cup engaging surface 294. The male taper 297 can include any appropriate angle relative to a central or concentric axis of the second liner 216. The angle of the male taper 297 can be substantially identical or similar to an angle provided by a female taper 266 of the acetabular cup 212. The tapers 297 and 266 can include selected angles, such as about 1° to about 45°. The angles can allow the male taper 297 to engage the female taper 266 in a substantially locked or connected manner, such as with a Morse taper. The interconnection of the tapers 297 and 266 can allow a fixation of the second liner 216 into the cup cavity 242 of the acetabular cup 212 at a selected time.

During assembly of the second liner 216 with the acetabular cup 212, a surgeon can generally align the projection 299 of the second liner 216 into the apical hole 248 of the acetabular cup 212.

Turning now to FIGS. 16-22, an acetabular prosthesis assembly constructed in accordance to another example of the present teachings is shown and generally identified at reference numeral 310. The acetabular prosthesis assembly 310 can generally include a single acetabular cup 312 that can be selectively and alternatively interconnected with a first bearing or liner 314, a second bearing or liner 316 or a third bearing or liner 318. In one example, the first liner 314 can be formed of any appropriate material, such as polymers, including UHMWPE or PEEK. The second liner 316 can be formed of a substantially or relatively hard or rigid material, such as a metal material described above with respect to the second liner 16. The third liner 318 can be formed of a substantially or relatively hard or rigid material, such as a ceramic material. In one example, the second and third liners 316 and 318 can have an equivalent geometry. As such, the second and third liners 316 and 318 have been denoted in the drawings simply as a single liner. As with the acetabular prosthesis assembly 10 described above, the acetabular prosthesis assembly 10 allows for preoperative or intraoperative selection of various liners for alternatively positioning within the acetabular cup 312. In this way, the first, second and third liners 314, 316 and 318 can each engage a common acetabular cup 312 therefore minimizing the number of required components for a procedure.

With specific reference to FIGS. 16-19, the acetabular cup 312 will be described in greater detail. The acetabular cup 312 can be formed of biocompatible metallic material, such as described above with respect to the acetabular cup 12. The acetabular cup 312 can generally include a hemispherical body 320 having an inner liner engaging surface 322 and an outer bone engaging surface 324. The outer bone engaging surface 324 can have a porous metal coating 326. The acetabular cup 312 can include an upper rim 330 that extends between the inner liner engaging surface 322 and the outer bone engaging surface 324. Positioned near the upper rim 330 and above a plane 331 (FIG. 22) can be a connection area 332 including a groove 334. The groove 334 can receive or interconnect with a locking or connecting member 336. The connecting member 336 can cooperate with a locking groove 338 formed around the first liner 314 to assist in interconnecting the first liner 314 with the acetabular cup 312. The respective grooves 334 and 338 can be sized in any appropriate manner to receive or cooperate with the connecting member 336, such as in the Ringloc® Acetabular Implant sold by Biomet Manufacturing Corp. of Warsaw, Ind., USA.

The acetabular cup 312 can further include anti-rotation projections 340 and associated depressions 342 to assist in minimizing or eliminating rotation of the first liner 314 relative to the acetabular cup 312 after implantation. Also formed around the upper rim 330 can be a first and a second notch 343a and 343b (FIG. 19) configured to accept portions of the connecting member 336 as will be described herein. The inner liner engaging surface 322 of the acetabular cup 312 can define a cup cavity 344 that starts below the connection area 332 and below the plane 331. The acetabular cup 312 can include an apical portion 346 having an apical hole 348 that passes entirely through the acetabular cup 312.

Figure 16:
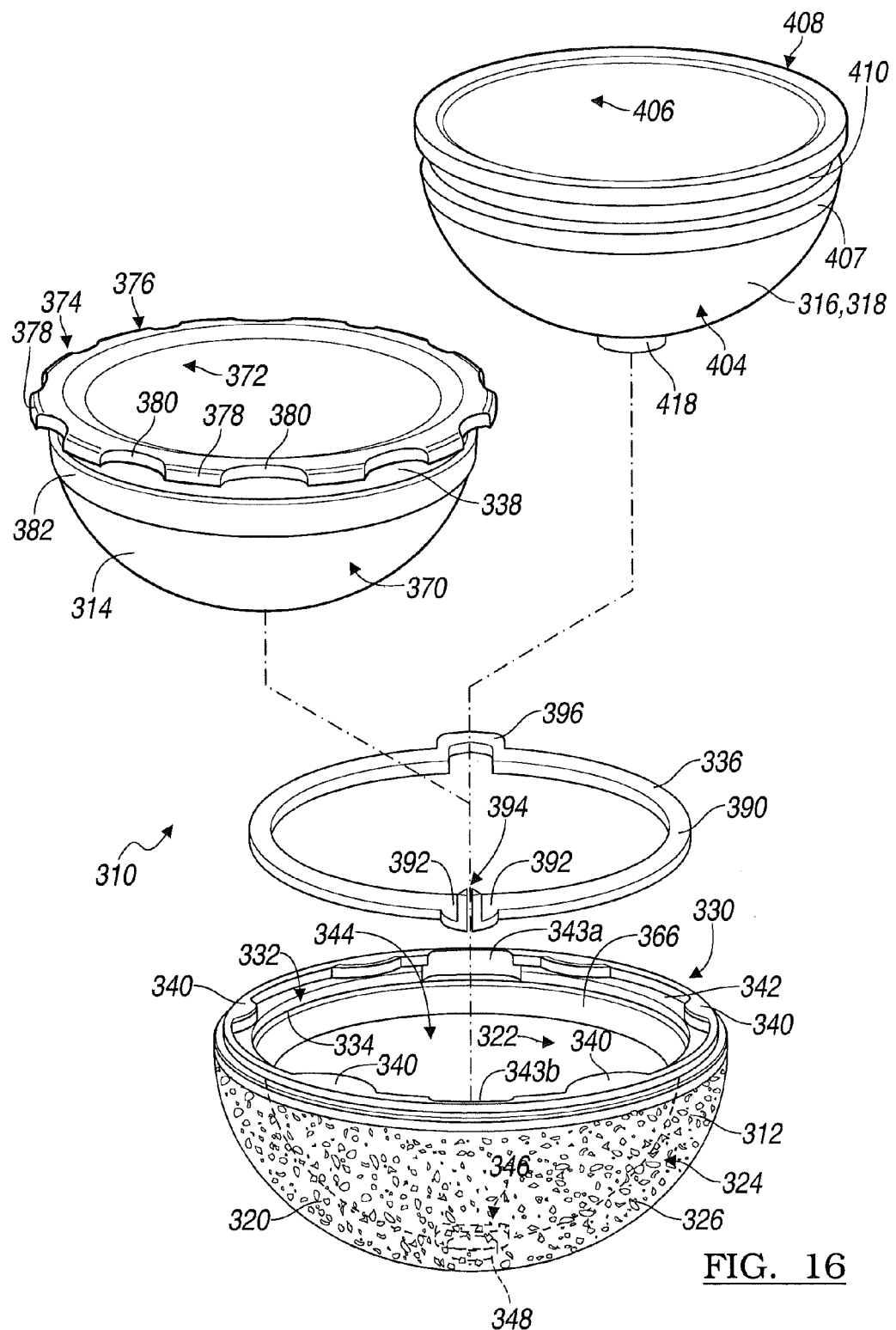
FIG. 16 is a perspective exploded view of an acetabular prosthesis assembly according to another example of the present teachings.
Figure 17:
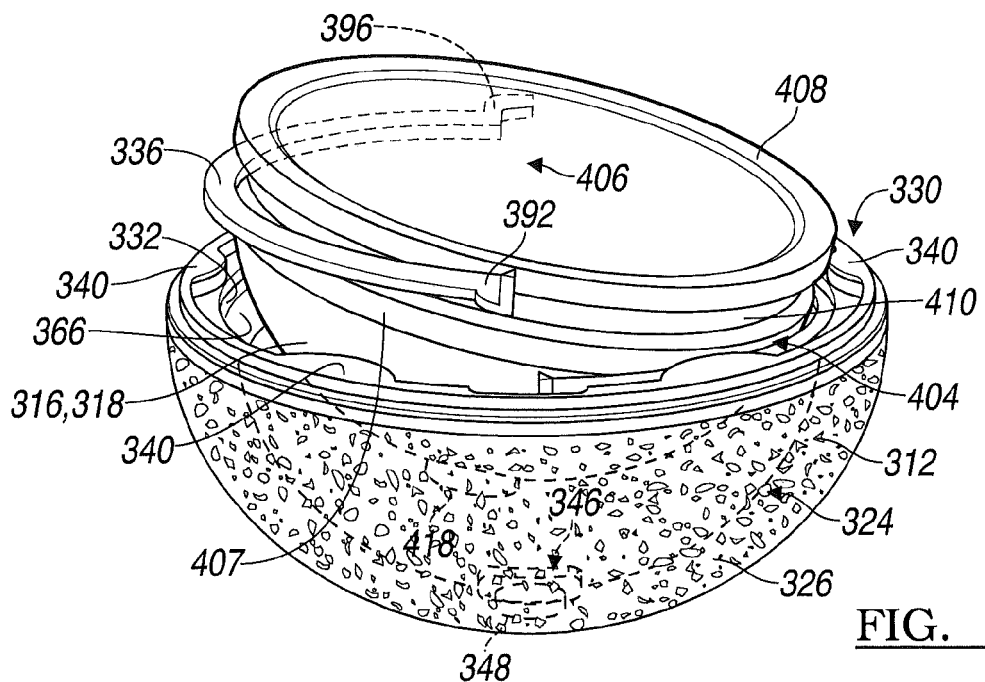
FIG. 17 is a perspective exploded view of the acetabular cup and second liner shown with a connecting member partially cooperating with the acetabular cup and partially cooperating with the second liner for illustrative purposes during an assembly step.
Figure 18:
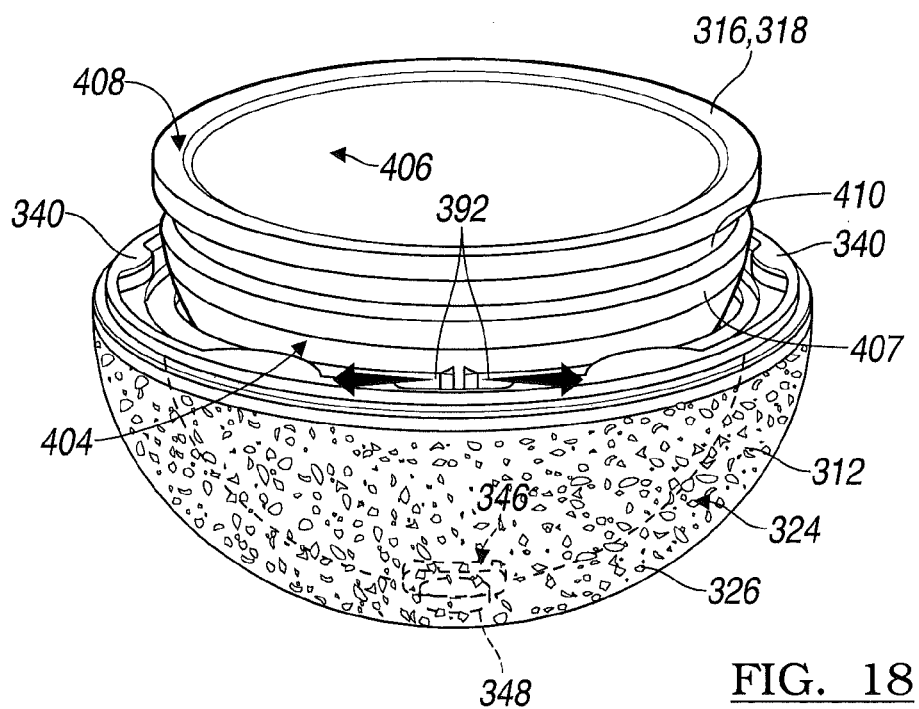
FIG. 18 is a perspective partial exploded view of the acetabular cup and connecting member shown during receipt of the second liner during an exemplary assembly sequence.
Figure 19:
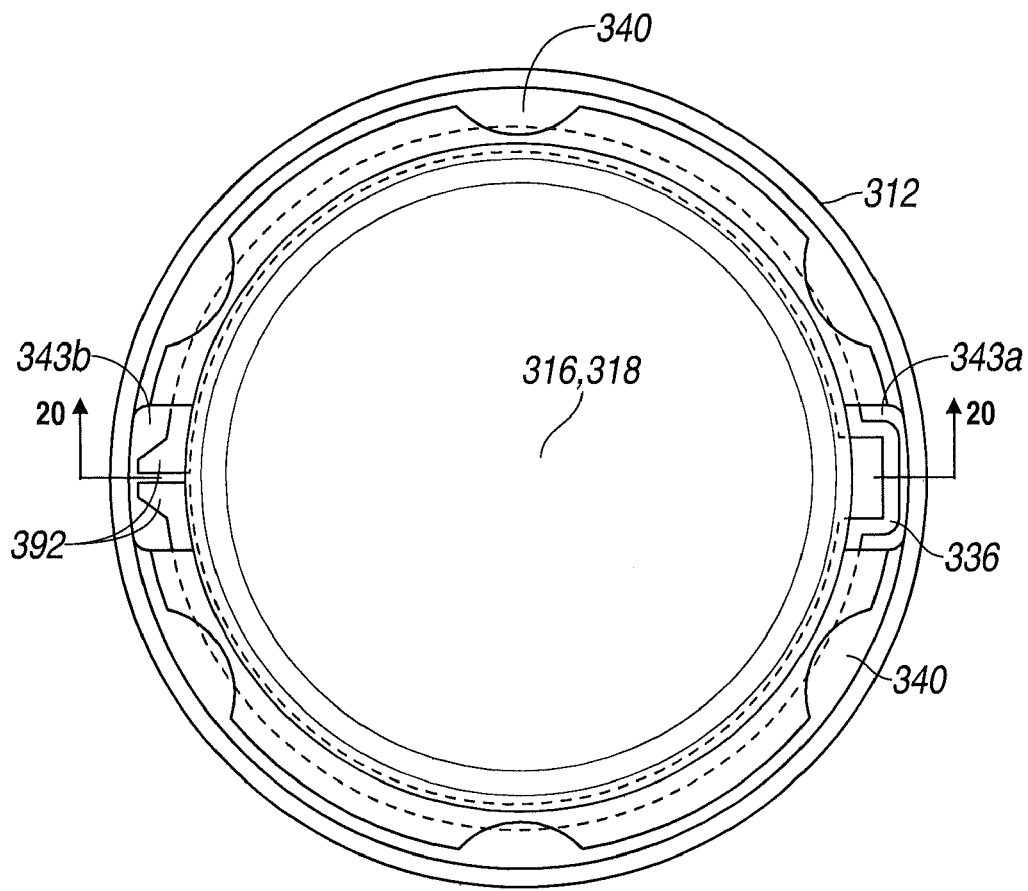
FIG. 19 is a perspective view of the acetabular cup, connecting member and second liner shown in an assembled position.
Figure 20:
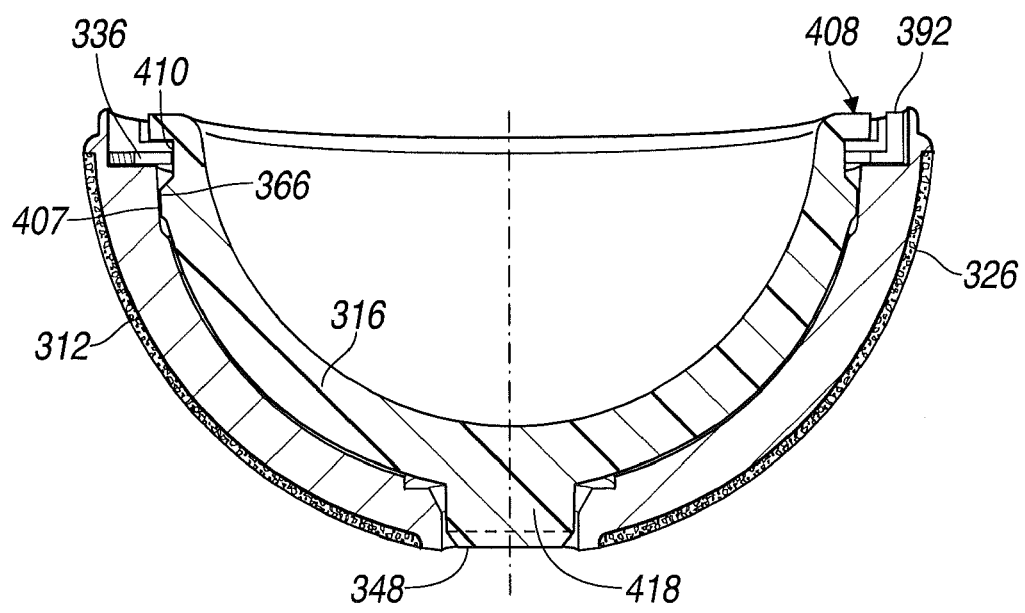
FIG. 20 is a cross-sectional view of the assembled acetabular cup, connecting member and second liner taken along line 20-20 of FIG. 19.
Figure 21:
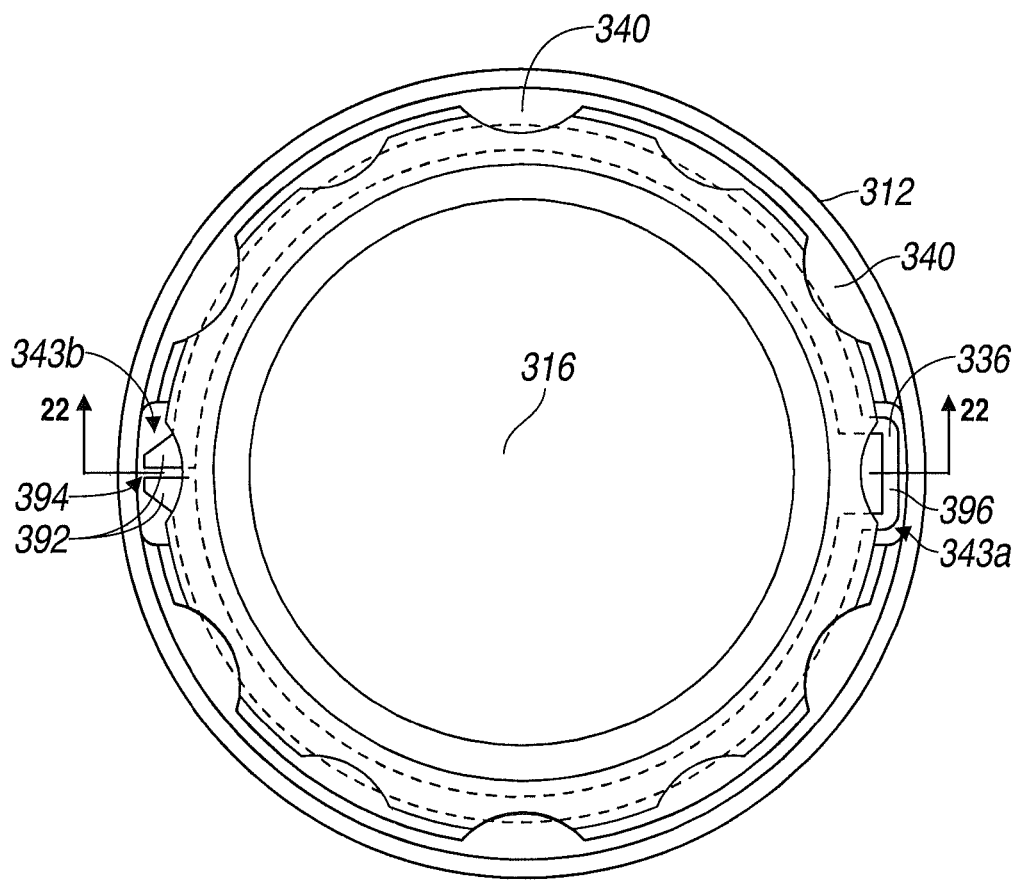
FIG. 21 is a perspective view of the acetabular cup, connecting member and first liner of FIG. 16 and shown in an assembled position.

With reference now to FIGS. 16, 21 and 22, the first liner 314 according to one example will be described in greater detail. The first liner 314 can include an outer cup engaging surface 370 and an articulation or internal surface 372 for articulation relative to a femoral implant or a natural femoral head. The outer cup engaging surface 370 of the first liner 314 can also engage the inner liner engaging surface 322 of the acetabular cup 312 in an appropriate manner (FIG. 22), such as a substantially fixed or non-moving manner. The first liner 314 can include a liner connection portion 374 formed around an upper rim 376. The liner connection portion 374 can include a series of alternating anti-rotation tabs 378 and associated depressions 380 formed around the upper rim 376. A male taper 382 can be formed near the upper rim 376, such as at an area below the groove 338.

The connecting member 336 can generally include a ring-like body 390 having a pair of fingers 392 extending upright from a plane of the body 390. The fingers 392 can be located at a slot 394 formed in the body 390. Diametrically opposing the fingers 392 can be an outset tab 396. In one example, the connecting member 336 can be formed of PEEK or similar material. In one example, the connecting member 336 can be injection molded allowing for improved customization during a manufacturing process. By providing an injection molded connecting member 336, such as formed of PEEK, a cost savings can be realized over a traditional locking member that may be manufactured from metallic materials. One benefit of using a connecting member 336 formed of PEEK is that it will not allow any fretting corrosion when in contact with a liner made of metallic material (such as the second liner 316 as will be later described). In addition, a connecting member 336 being formed of PEEK can be easily cut or ruptured with a surgical instrument allowing for easy liner removal, such as during a revision procedure. For example, as shown in FIG. 21, a surgeon can gain access to the connecting member 336, such as at the first notch 343a and break or separate the connecting member 336 with a tool.

The second liner 316 and third liner 318 can be constructed similarly to the second and third liners 16 and 18 described above. The second liner 316 can generally include an outer cup engaging surface 404 and an internal articulating surface 406. A male taper 407 can be formed near an upper rim 408 of the second liner 316. A groove 410 can be formed proximate to the upper rim 408. The male taper 407 can include any appropriate angle relative to a central or concentric axis of the second liner 316. As with the other male tapers described herein, the male taper 407 can be substantially identical or similar to an angle provided by a female taper 366 of the acetabular cup 312. A projection 418 can be formed at an apex of the second liner 316 that extends proud from the outer cup engaging surface 404. The projection 418 can generally be received within the apical hole 348 provided on the acetabular cup 312 in an assembled position for alignment purposes.

The acetabular cup 312 can be implanted into an acetabulum, such as described above with respect to the acetabular cup 12. Assembly of the first liner 314 to the acetabular cup 312 according to one example will now be described. At the outset, a surgeon can align the connecting member 336 for receipt into the groove 334 of the acetabular cup 312. In one example of installing the connecting member 336 into the groove 334 of the acetabular cup 312, the outset tab 396 can be positioned into the notch 343a while the body 390 of the connecting member 336 is compressed and manipulated into the groove 334.

In another method of assembly, the connecting member 336 can be first installed onto the groove 338 of the first liner 314 or the groove 410 of the second liner 316. In either scenario, a surgeon can press the respective liners 314, 316 or 318 into the acetabular cup 312 and the connecting member 336 can compress or expand to allow it to pass over a portion of the acetabular cup 312 or the respective liners 314, 316 or 318 and expand into the respective grooves 334 and 338. The connecting member 336 is shown in two pieces in FIG. 17 to illustrate how it can either first be engaged to the acetabular cup 312 or to the respective liner (the second liner 316 shown). It is appreciated however that the connecting member 336 is one-piece. The connecting member 336 includes a width that is great enough to engage both of the groove 334 in the acetabular cup 12 and the groove 338 in the first liner 314 (and the groove 410 in the second and third liners 316, 318). Therefore, the connecting member 336 can fixedly hold the respective liners 314, 316 and 318 relative to the acetabular cup 312, at least in an axial position. When assembling the first liner 314, the anti-rotation projections 340 of the acetabular cup 312 can locate within selected depressions 380 formed around the upper rim 376 of the first liner 314. It is appreciated that while six anti-rotation projections 340 are illustrated around the rim 330 of the acetabular cup 312 and twelve depressions 380 are illustrated around the upper rim 376 of the first liner 314, the quantity of these features is merely exemplary and other configurations may be used.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An acetabular prosthesis assembly comprising:
an acetabular cup having an outer surface, an inner surface and an upper rim extending between the outer surface and the inner surface, the acetabular cup having a cup connection portion including an inner wall offset from an outer wall by a groove formed on an upper face of the upper rim, wherein an undercut is formed in the groove on one of the inner wall or outer wall; and
a first liner having an outer cup engaging surface and a liner connection portion that extends from a flange of the first liner, the liner connection portion having a finger that is received by the groove that selectively couples the liner connection portion with the cup connection portion in an assembled position;
wherein the first liner includes a protrusion extending from the finger that nests in the undercut formed in the groove of the acetabular cup in the assembled position;
wherein the cup connection portion and liner connection portion include a plurality of alternating inset and outset portions that cooperatively mate in the assembled position.

2. The acetabular prosthesis assembly of claim 1 wherein the groove extends uninterrupted annularly around the upper rim.

3. The acetabular prosthesis of claim 1 wherein the inner wall and the outer wall are generally parallel to an axis through an apex of the acetabular cup.

4. The acetabular prosthesis assembly of claim 1 wherein the acetabular cup further comprises an anti-rotation counterbore defined by the inner liner engaging surface and wherein the first liner includes an anti-rotation projection extending from the outer cup engaging surface that cooperatively locates at the anti-rotation counterbore of the acetabular cup in the assembled position.

5. The acetabular prosthesis assembly of claim 1, wherein the first liner is formed of polyethylene.

6. The acetabular prosthesis assembly of claim 1, further comprising:
a second liner formed of metal, the second liner having a male tapered portion that selectively engages a complementary female tapered portion formed on the inner surface of the acetabular cup in an assembled position; and
a third liner formed of ceramic and having a male tapered portion that selectively engages the female tapered portion on the inner surface of the acetabular cup in an assembled position;
wherein the acetabular cup selectively and alternatively mates with any of the first, second or third liners.

7. An acetabular prosthesis assembly comprising:
an acetabular cup having an outer bone engaging surface, an inner liner engaging surface, and a cup connection portion formed into an upper rim, the cup connection portion collectively formed by an inner wall and an outer wall offset by an annular groove in the upper rim, wherein a portion of the inner liner engaging surface is common to the inner wall and a portion of the outer bone engaging surface is common to the outer wall, wherein the acetabular cup further comprises an anti-rotation counterbore defined by the inner liner engaging surface and a threaded bore located within the anti-rotation counterbore that passes entirely through the acetabular cup; and
a first liner having an outer cup engaging surface and a liner connection portion that extends from a flange of the first liner, the liner connection portion having an annular finger that is received by the annular groove of the acetabular cup that selectively couples the liner connection portion with the cup connection portion in an assembled position.

8. The acetabular prosthesis assembly of claim 7 wherein the anti-rotation counterbore includes a series of alternating inset and outset portions.

9. The acetabular prosthesis assembly of claim 7 wherein the first liner includes an anti-rotation projection extending from the outer cup engaging surface that cooperatively locates at the anti-rotation counterbore of the acetabular cup in the assembled position.

10. The acetabular prosthesis assembly of claim 9 wherein the anti-rotation projection defines a series of inset and outset portions that cooperatively mate with corresponding inset and outset portions of the acetabular cup in the assembled position.

11. The acetabular prosthesis assembly of claim 7 wherein the inner liner engaging surface defines a cup cavity and wherein the cup connection portion is formed outside of the cup cavity.

12. The acetabular prosthesis assembly of claim 7 wherein the inner wall includes an undercut formed from the annular groove.

13. The acetabular prosthesis assembly of claim 12 wherein the undercut is formed into one of the inner wall or the outer wall.

14. The acetabular prosthesis assembly of claim 12 wherein the first liner includes a protrusion extending from the annular finger that nests in the undercut of the acetabular cup in the assembled position.

15. The acetabular prosthesis assembly of claim 14 wherein the annular finger is flexible such that the annular finger flexes radially outwardly during advancement of the liner around the inner wall until the protrusion reaches the undercut of the acetabular cup in the assembled position.

16. The acetabular prosthesis assembly of claim 14 wherein the annular finger includes at least one relief notch formed therein.

17. The acetabular prosthesis assembly of claim 7, wherein the first liner is formed of polyethylene.

18. The acetabular prosthesis assembly of claim 7, further comprising:
a second liner formed of cobalt-chromium, the second liner having a male tapered portion that selectively engages a complementary female tapered portion formed on the inner liner engaging surface of the acetabular cup in an assembled position; and
a third liner formed of ceramic and having a male tapered portion that selectively engages the female tapered portion on the inner liner engaging surface of the acetabular cup in an assembled position;
wherein the acetabular cup selectively and alternatively mates with any of the first, second or third liners.

19. An acetabular prosthesis assembly comprising:
an acetabular cup having an outer bone engaging surface, an inner liner engaging surface and an upper rim extending between the outer bone engaging surface and the inner liner engaging surface, the acetabular cup having a cup connection portion including an annular groove formed between inner and outer walls on an upper face of the upper rim, one of the inner and outer walls having an undercut formed from the groove; and
a liner having an outer cup engaging surface and a liner connection portion including a protrusion extending from a finger that extends from a flange of the first liner, the finger being received by the groove formed on the upper face of the acetabular cup whereby the protrusion locates beneath the undercut and selectively couples the liner connection portion with the cup connection portion in an assembled position;
wherein the cup connection portion and liner connection portion include a plurality of alternating inset and outset portions that cooperatively mate in the assembled position.

* * * * *